US007772251B2

(12) United States Patent
Stürzebecher et al.

(10) Patent No.: US 7,772,251 B2
(45) Date of Patent: Aug. 10, 2010

(54) N-SULPHONYLATED AMINO ACID DERIVATIVES, METHOD FOR THE PRODUCTION AND USE THEREOF

(75) Inventors: Jörg Stürzebecher, Erfurt (DE); Torsten Steinmetzer, Jena (DE); Andrea Schweinitz, Jena (DE); Anne Stürzebecher, Weimar (DE); Kerstin Uhland, Gräfelfing (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 641 days.

(21) Appl. No.: 10/555,821

(22) PCT Filed: May 17, 2004

(86) PCT No.: PCT/EP2004/005291

§ 371 (c)(1),
(2), (4) Date: Aug. 8, 2006

(87) PCT Pub. No.: WO2004/101507

PCT Pub. Date: Nov. 25, 2004

(65) Prior Publication Data

US 2007/0055065 A1 Mar. 8, 2007

(30) Foreign Application Priority Data

May 16, 2003 (DE) ................. 103 22 191

(51) Int. Cl.
*A61K 31/445* (2006.01)
*A61K 31/495* (2006.01)
*C07D 211/26* (2006.01)

(52) U.S. Cl. ................. 514/316; 514/255; 514/319; 514/325; 514/330; 544/360; 546/203; 546/204; 546/205; 546/226

(58) Field of Classification Search ................. 514/319, 514/330, 255, 316, 325; 546/205, 226, 203, 546/204; 544/360
See application file for complete search history.

(56) References Cited

U.S. PATENT DOCUMENTS 6,624,169 B1 * 9/2003 Wilhelm et al. ........ 514/255.01

FOREIGN PATENT DOCUMENTS

| CH | 689 611 | | 3/1995 |
|---|---|---|---|
| CH | 689 611 | A5 | 7/1999 |
| WO | WO 92/08709 | | 3/1992 |
| WO | WO 92/08709 | | 5/1992 |
| WO | WO 94/18185 | | 8/1994 |
| WO | WO 00/04954 | | 2/2000 |
| WO | WO 00/17158 | | 3/2000 |
| WO | WO 01/97794 | | 12/2001 |
| WO | WO 01/97794 | A2 | 12/2001 |
| WO | WO 02/20475 | | 3/2002 |
| WO | WO 02/20475 | A2 | 3/2002 |
| WO | WO 03/070229 | | 8/2003 |
| WO | WO 03/070229 | A2 | 8/2003 |

OTHER PUBLICATIONS

Wilhelm et al. "preparation and use . . . " CA 132:108297 (2000).*
Wilkstroem et al. "prparation of 2-amidino . . . " CA 132:222869 (2000).*
Renatus et al. "Structural and functional . . . " J. Med. Chem. v.41, p. 5445-5456 (1998).*
Rubini et al. "Synthesis of isosteri . . . " Tetrhedron v. 42, p. 6039-6045 (1986).*
Patani et al. "Bioisosterism . . . " Chem. Rev. v.96, p. 3147-3148, 3170 (1996).*
Stuerzebecher et al. "Piperazine of . . . " CA 122:161363 (1995).*
Coussens et al., "Matrix Metalloproteinase Inhibitors and Cancer: Trials and Tribulations," *Science* 295:2387-2392 (2002).
Dexter et al., "N,N-Dimethylformamide-Induced Alteration of Cell Culture Characteristics and Loss of Tumorigenicity in Cultured Human Colon Carcinoma Cells," *Cancer Research* 39:1020-1025 (1979).
Dixon et al., "The Determination of Enzyme Inhibitor Constants," *Biochem J.* 55:170-171 (1953).
Enyedy et al., "Structure-Based Approach for the Discovery of Bis-Benzamidines as Novel Inhibitors of Matriptase," *J. Med. Chem.* 44:1349-1355 (2001).
Friedrich et al., "Catalytic Domain Structures of MT-SP1/Matriptase, a Matrix-Degrading Transmembrane Serine Proteinase," *The Journal of Biological Chemistry* 277:2160-2168 (2002).
Hooper et al., "Type II Transmembrane Serine Protease," *The Journal of Biological Chemistry* 276:857-860 (2001).
Ihara et al., "Prometastatic Effect of N-Acetylglucosaminyltransferase V is Due to Modification and Stabilization of Active Matriptase by Adding β1-6 GlcNAc Branching," *The Journal of Biological Chemistry* 277:16960-16967 (2002).
Kang et al., Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer, *Cancer Research* 63:1101-1105 (2003).
Lee et al., "Activation of Hepatocyte Growth Factor and Urokinase/Plasminogen Activator by Matriptase, an Epithelial Membrane Serine Protease," *The Journal of Biological Chemistry* 275:36720-36725 (2000).
Lin et al., "Purification and Characterization of a Complex Containing Matriptase and a Kunitz-type Serine Protease Inhibitor from Human Milk," *The Journal of Biological Chemistry* 274:18237-18242 (1999).
Lin et al., "Molecular Cloning of cDNA for Matriptase, a Matrix-Degrading Serine Protease with Trypsin-Like Activity," *The Journal of Biological Chemistry* 274:18231-18236 (1999).

(Continued)

*Primary Examiner*—Celia Chang
(74) *Attorney, Agent, or Firm*—Clark & Elbing LLP

(57) ABSTRACT

The present invention relates to N-sulfonylated amino acid derivatives, where an aryl radical is linked via the sulfonyl group N-terminally to the amino acid and a radical which comprises at least one imino group and at least one further basic group which represents an optionally modified amino, amidino or guanidino group is linked C-terminally via the carbonyl group. The invention likewise relates to processes for preparing these compounds and to their use, in particular as inhibitors of matriptase.

27 Claims, 2 Drawing Sheets

OTHER PUBLICATIONS

Lin et al., "Characterization of a Novel, Membrane-bound, 80-kDa Matrix-Degarding Protease From Human Breast Cancer Cells," *The Journal of Biological Chemistry* 272:9147-9152 (1997).

Long et al., "Synthesis and Evaluation of the Sunflower Derived Trypsin Inhibitor as a Potent Inhibitor of the Type II Transmembrane Serine Protease, Matriptase," *Biorganic & Medicinal Chemistry Letters* 11:2515-2519 (2001).

Oberst et al., "Expression of the Serine Protease Matriptase and Its Inhibitgor HAI-I in Epithelial Ovarian Cancer: Correlation with Clinical Outcome and Tumor Clinicopathological Parameters," *Clinical Cancer Research* 8:1101-1107 (2002).

Shi et al., "Identification and Characterization of a Novel Matrix-Degrading Protease from Hormone-Dependent Human Breast Cancer Cells," *Cancer Research* 53:1409-1415 (1993).

Stürzebecher et al., "3-Amidinophenylalanine-Based Inhibitors of Urokinase," *Bioorganic & Medicinal Chemistry Letters* 9:3147-3152 (1999).

Sucker et al., "Pharmazeutische Technologie," Georg Thieme Verlag Stuttgart, New York, 1991.

Takeuchi et al., "Reverse Biochemisty: Use of Macromolecular Protease Inhibitors to Dissect Complex Biological Processes and Identify a Membrane-Type Serine Protease in Epithelial Cancer and Normal Tissue," *Proc. Natl. Acad. Sci.* 96:11054-11061 (1999).

Takeuchi et al., "Cellular Localization of membrane-Type Serine Protease 1 and Identification of Protease-Activated Receptor-2 and Single chain Urokinase-Type Plasminogen Activator as Substrates," *The Journal of Biological Chemistry* 275:26333-26342 (2000).

Zeslawska et al., "Crystals of the Urokinase Type Plasminogen Activator Variant βc-uPA in Complex with Small Molecule Inhibitors Open the Way towards Structure-Based Drug Design," *J. Mol. Boil.* 301:465-475 (2000).

Zhang et al., "Assignment of Human Putative Tumor Suppressor Genes ST13 (Alias SNC6) and ST14 (Alias SNC19) to Human Chromosome Bands 22q13 and 11q24 →q25 by in Situ Hybridization," *Cytogenet Cell Genet* 83:56-57 (1998).

Bauer, "Hilfsstoffe," in *Pharmazeutische Technologie.* Sucker et al. (eds.), Georg Thieme Verlag Stuttgart: New York, p. 174-216 (1991).

Hooper et al., "Type II Transmembrane Serine Proteases," *J. Biol. Chem.* 276:857-860 (2001).

* cited by examiner

+25 ng/ml proHGF    +12.5 ng/ml proHGF

+ pro-HGF

+ pro-HGF + Inhibitor 54

+ pro-HGF + Inhibitor 37

N-SULPHONYLATED AMINO ACID DERIVATIVES, METHOD FOR THE PRODUCTION AND USE THEREOF

CROSS REFERENCE TO RELATED APPLICATIONS

This application is the U.S. National Stage of International Application No. PCT/EP2004/005291, filed May 17, 2004, which claims benefit of German Application No. 10322191.3, filed May 16, 2003, hereby incorporated by reference.

The present invention relates to N-sulfonylated amino acid derivatives, where an aryl radical is linked via the sulfonyl group N-terminally to the amino acid and a radical which comprises at least one imino group and at least one further basic group which represents an optionally modified amino, amidino or guanidino group is linked C-terminally via the carbonyl group. The invention likewise relates to processes for preparing these compounds and to their use, preferably as medicaments and in this connection in particular as inhibitors of matriptase.

Proteases regulate numerous physiological processes which enable or stimulate the growth and metastasis of tumor cells. This relates in particular to the proteolytic degradation of the extracellular matrix proteins which surround the tumor cells, the degradation making it possible for the tumor cells which have migrated from tumors to invade adjoining tissues and the lymphatic and blood systems. Proteases are also involved in the activation of growth factors which, for example, stimulate the proliferation of tumor cells or angiogenesis and thus make tumor growth possible. These proteolytic enzymes include various matrix metalloproteases, membrane-bound metalloproteases, lysosomal cysteine proteases and a large number of serine proteases such as, for example, urokinase, plasmin, elastase, thrombin or cathepsin G, and also the type II transmembrane serine protease matriptase or MT-SP1 (Hooper et al., J. Biol. Chem. 276, 857-860, 2001).

There have been numerous attempts to inhibit the growth and metastasis of tumors through the use of protease inhibitors, but experiments with inhibitors of matrix metalloproteases have shown hardly any effect in clinical studies (Coussens et al., Science 295, 2387-2392, 2002). Initial clinical investigations with inhibitors of urokinase have also now been initiated, but no results on their efficacy are known as yet.

Matriptase is a trypsin-like serine protease which was originally isolated from breast cancer cells and preferentially cleaves C-terminally peptide linkages of the basic amino acid arginine (Shi et al., Cancer Res. 53, 1409-1415, 1993; Lin et al., J. Biol. Chem. 272, 9147-9152, 1997).

In 1998, the matriptase gene was cloned as putative tumor suppressor by a subtractive hybridization method in which healthy and carcinogenic intestinal tissue were used (Zhang et al. Cytogenet. Cell Genet. 83, 56-57, 1998).

Matriptase and MT-SP1 (abbreviation for "membrane-type serine protease 1) (Takeuchi et al., Proc. Natl. Acad. Sci. USA 96, 11054-11061, 1999; Takeuchi et al., J. Biol. Chem. 275, 26333-26342, 2000) have the same cDNA. However, owing to alternative splicings, the protein sequence of matriptase is truncated at the N terminus by 172 amino acids compared with MT-SP1. The gene for MT-SP1 was isolated from an epithelial cell line of a prostate tumor.

In the context of the present invention, the term "matriptase" refers to every trypsin-like protein having a molecular weight of from 72 to 92 kDa which is derived from the gene sequences having the entry number AF118224, AF133086, BANKIt25705.0 and NM021978 (GenBank/EBI Data Bank) and has been described previously (Takeuchi et al., Proc. Natl. Acad. Sci. USA 96, 11054-11061, 1999; Lin et al., J. Biol. Chem. 274, 18231-18236, 1999). The term "matriptase" refers in particular to both the single-chain and two-chain forms of the protein. The zymogenic, inactive form of matriptase is a single-chain protein. The two-chain form of matriptase is its active form having catalytic activity. In the context of the present invention therefore the term "matriptase" refers in particular to the original matriptase described hereinbefore, as well as MT-SP1.

The enzyme is tethered by means of a transmembrane domain in the membrane of epithelial or cancer cells, with the serine protease domain of matriptase being located on the cell surface and thus in the extracellular space (Hooper et al., J. Biol. Chem. 276, 857-860, 2001). It has therefore been supposed that matriptase might be involved in the proliferation and metastasis of breast cancer cells through degradation and transformation of extracellular matrix proteins, in the activation of latent growth factors and other proteolytic cascades (Shi et al., Cancer Res. 53, 1409-1415, 1993; Lin et al., J. Biol. Chem. 272, 9147-9152, 1997).

It has also been possible to isolate matriptase from human milk but, in this case, it was in the form almost entirely of a proteolytically inactive complex with the endogenous inhibitor HAI-1 (Lin et al., J. Biol. Chem. 274, 18237-18242, 1999). In contrast thereto, matriptase from breast cancer cells is very substantially in an uncomplexed and thus catalytically active form, and only a small part is bound to HAI-1.

The first potential substrates of matriptase have now been described. Matriptase is able to activate hepatocyte growth factor (HGF) which is also referred to as scattering factor (Lee et al., J. Biol. Chem. 275, 36720-36725, 2000). Pro-HGF is secreted by cancer cells or stromal cells in inactive form as single-chain protein and is converted in the extracellular space by cleavage C-terminally of the Arg495 into the active two-chain form (HGF). Binding of HGF results in the cell surface receptor c-Met being activated and phosphorylated on particular tyrosine residues. It has recently been demonstrated that there is a close correlation between a high expression of c-Met, matriptase and HAI-1 and a poor prognosis for breast cancer patients (Kang et al., Cancer Res. 63, 1101-1105, 2003). It has also been possible to show in the investigation of ovarian tumors that matriptase is expressed to an increased extent. It was moreover found that matriptase is expressed almost exclusively without HAI-1 especially in advanced tumors of type III/IV, in contrast to tumors of type I/II. This indicates that in the advanced stage there is an imbalance between matriptase and the inhibitor HAI-1, thus enhancing the proteolytic activity of matriptase and thereby probably also the invasive potential of the tumor cells (Oberst et al., Clin. Cancer Res. 8, 1101-1107, 2002).

Besides activation of Pro-HGF, matriptase is possibly also involved in activation of the plasminogen activator cascade. Thus, matriptase is able to activate pro-urokinase to urokinase (uPA) (Lee et al., J. Biol. Chem. 275, 36720-36725, 2000; Takeuchi et al., J. Biol. Chem. 275, 26333-26342, 2000) which converts plasminogen into plasmin. Plasmin is the principal activator of matrix metalloproteases which are involved in the degradation of extracellular matrix proteins, which is also regarded as a precondition for metastasis.

Ihara et al. (J. Biol. Chem. 277, 16960-16967, 2002) were able to show that stomach cancer cells show enhanced expression of β1-6-N-acetylglucosaminyltransferase (GnT-V) which is able to glycosylate matriptase. This modification makes matriptase more stable to degradation and is present in proteolytically active form in increased concentration.

It can be inferred from these findings that development of an effective and selective inhibitor of matriptase will make it possible to inhibit the proliferation of tumors and their metastasis. Although it has now been possible also to elucidate the X-ray structure of the catalytic domain of matriptase complexed with benzamidine and with the bovine pancreatic trypsin inhibitor, to date only a few inhibitors of matriptase are known (Friedrich et al., J. Biol. Chem. 277, 2160-2168, 2002).

Enyedy et al. (J. Med. Chem. 44, 1349-1355, 2001) described bis-benzamidines where the most effective inhibitor has a $K_i$ of 0.19 μM.

WO 01/97794 describes a method for inhibiting progression of carcinoma in which matriptase plays a part. The compounds employed in this case comprise two groups able to carry a positive charge at a physiological pH. These groups are moreover connected together by a chemical structural unit which has a length of from 5 to 30, preferably 15 to 24 Angstrom. Positively charged groups which are disclosed are the amino, amidino, guanidino groups and a cyclic group derived from the amidino or guanidino group. Amino acid derivatives are not mentioned in WO 01/97794 and accordingly in particular no sulfonylated amino acid derivatives. On the contrary, the compounds explicitly disclosed in WO 01/97794 differ fundamentally from the compounds claimed in the context of the present invention.

Tripeptide aldehydes having C-terminal arginal are published in WO 02/20475. After preincubation of matriptase with these inhibitors for a period of 30 minutes, $IC_{50}$ values of less than 100 nM were determined for the most effective compounds, although exact inhibitory constants were not stated. It is believed that these inhibitors bind covalently to matriptase to form a hemiacetal. In the case of the development of inhibitors for other trypsin-like serine proteases such as, for example, thrombin or factor Xa, however, it has been shown that such transition state-analogous peptide aldehydes are unsuitable for developing an active substance which can be employed medicinally.

Long et al. (Bioorganic. Med. Chem. Lett. 11, 2515-2519, 2001) have described the synthesis of a bicyclic peptide of 14 amino acids which was originally isolated from sunflower seed. The peptide inhibits matriptase with an inhibitory constant of 0.92 nM, but it must be assumed that these structures are unsuitable for developing an active substance.

One of the objects on which the present invention is based was therefore to provide an active substance which is also suitable for therapeutic applications and which inhibits matriptase with high activity and specificity.

Accordingly, the present invention relates to a compound of the formula (I)

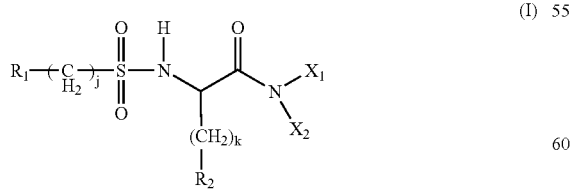

or a salt or a prodrug of this compound, where (a) $X_1$ and $X_2$ are independently of one another hydrogen or an alkyl radical having 1, 2 or 3 C atoms, and at least one of the radicals $X_1$ and $X_2$ is a radical of the structure (I')

where
optionally at least one of the methylene groups which are indexed with m or n in (I') is substituted at least once by a hydroxyl, a halogen, a pseudohalogen or a $COOR_2'$ group, and $R_2'$ is a linear, branched or cyclic alkyl group having 1 to 10 C atoms, and/or
optionally at least one of the C atoms of the methylene groups which are indexed with m or n in (I') is replaced by S, N or O, and/or
optionally at least one of the bonds forming the ring

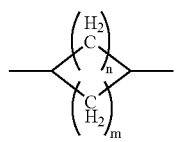

in (I') is a double bond, or where
(b) $X_1$ and $X_2$ are bridged to form a ring in such a way that the compound (I) has the structure (I")

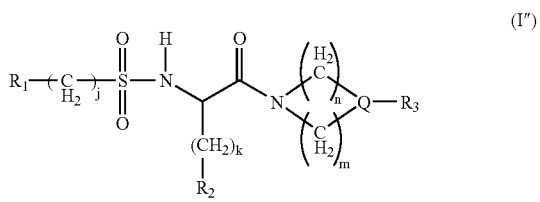

where
optionally at least one of the methylene groups which are indexed with m or n in (I") is substituted at least once by a hydroxyl, a halogen, a pseudohalogen or a $COOR_2'$ group, and $R_2'$ is a linear, branched or cyclic alkyl group having 1 to 10 C atoms, and/or
optionally at least one of the C atoms of the methylene groups which are indexed with m or n in (I") is replaced by S, N or O, and/or
with retention of the imino group C-terminally linked to the sulfonylated amino acid, optionally at least one of the bonds forming the ring

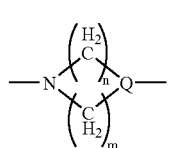

in (I") is a double bond, and where
(i) $R_1$ is an optionally partially hydrogenated aryl or heteroaryl group comprising at least one of the atoms O, N or S, having 5 to 20 C atoms, or a linear, branched or cyclic alkyl group having 1 to 10 C atoms, where $R_1$ is optionally substituted by at least one halogen and/or pseudohalogen group, and/or at least one linear, branched or cyclic alkyl or alkyloxy or alkylthio group having 1 to 10 C atoms, which is optionally substituted at least once by a halogen, pseudohalogen, hydroxyl, amino, cyano, amidino, guanidino or carboxyl group, where the carboxyl group is optionally esterified with a linear, branched or cyclic alkyl group having 1 to 10 C atoms, and where the linear, branched or cyclic alkyl group having 1 to 10 C atoms optionally comprises at least one heteroatom selected from the group consisting of O, N and S, and/or at least one aryl or heteroaryl group having 5 to 20 C atoms, where this aryl or heteroaryl group is optionally substituted by at least one linear, branched or cyclic alkyl group having 1 to 10 C atoms and/or at least one $COR_2'$ and/or $COOR_2'$ group, where $R_2'$ is a linear, branched or cyclic alkyl group having 1 to 10 C atoms, and/or at least one halogen group and/or at least one pseudohalogen group and/or at least one alkoxy group or one alkylthio group, where the alkyl radical has in each case 1 to 10 C atoms, and/or at least one nitro group and/or at least one haloalkyl group having 1 to 10 C atoms, and where the aryl or heteroaryl group is linked via an alkylene group having 1 to 3 C atoms or via an oxygen atom or a sulfur atom to the radical $R_1$;

at least one hydroxyl, amino, cyano, amidino, guanidino, carboxyl or carboxyalkyl group, where the amino group is optionally acylated and/or where the alkyl group of the carboxyalkyl group has 1 to 10 C atoms and/or the carboxyl group is optionally esterified with a linear, branched or cyclic alkyl group having 1 to 10 C atoms or is amidated;

(ii) $R_2$ is an at least monosubstituted aryl group having 1 to 10 C atoms, where optionally at least one of these C atoms is replaced by S, N or O, at least one substituent is a group according to $R_4$, $R_2$ is optionally additionally substituted by a hydroxyl, $COR_2'$ or $COOR_2'$ group, and $R_2'$ is a linear, branched or cyclic alkyl group having 1 to 10 C atoms;

(iii) $R_3$ is a radical of the following formula (II):

   (II)

where $A_1$ is either absent or an alkylene group having 1 to 4 C atoms which is optionally substituted by at least one halogen and/or pseudohalogen group and/or at least one linear, branched or cyclic alkyl group having 1 to 10 C atoms and/or at least one aryl or one aralkyl group having 5 to 10 C atoms and/or at least one cycloalkyl group having 3 to 10 C atoms and/or at least one hydroxyl, cyano, alkyloxy or alkylthio having 1 to 10 C atoms, carboxyl or carboxyalkyl group, where the alkyl group of the carboxyalkyl group has 1 to 10 C atoms, and/or the carboxyl group is optionally esterified with a linear, branched or cyclic alkyl radical having 1 to 10 C atoms, or is amidated;

T is either absent or one of the following groups:

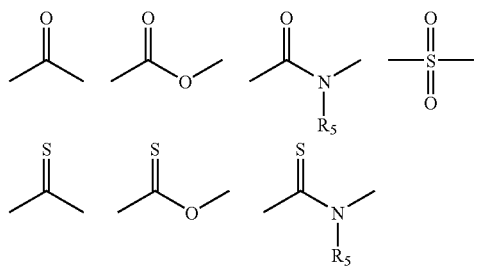

where $R_5$ is hydrogen or an alkyl group having 1 to 10 C atoms or an alkylene group having 1 to 6 C atoms, which forms with $A_2$ a ring optionally comprising at least one heteroatom;

where the amide or ester linkage can be incorporated in both orientations, that is to say the following orientations are also included:

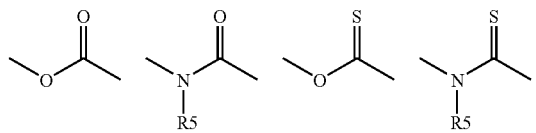

$A_2$ is a linear, branched or cyclic alkylene group having 1 to 10 C atoms or an aryl-, heteroaryl- or aralkylene group having 1 to 10 C atoms, optionally comprising at least one heteroatom selected from the group consisting of N, S and O, which is optionally substituted by at least one halogen and/or pseudohalogen group and/or at least one linear, branched or cyclic alkyl group having 1 to 10 C atoms and/or at least one aryl or one aralkyl group having 5 to 10 C atoms and/or at least one cycloalkyl group having 3 to 10 C atoms and/or at least one hydroxyl, cyano, alkyloxy or alkylthio group having 1 to 10 C atoms, carboxyl or carboxyalkyl group, where the alkyl group of the carboxyalkyl group has 1 to 10 C atoms, and/or the carboxyl group is optionally esterified with a linear, branched or cyclic alkyl radical having 1 to 10 C atoms, or is amidated;

(iv) $R_4$ is one of the following, optionally modified basic groups:

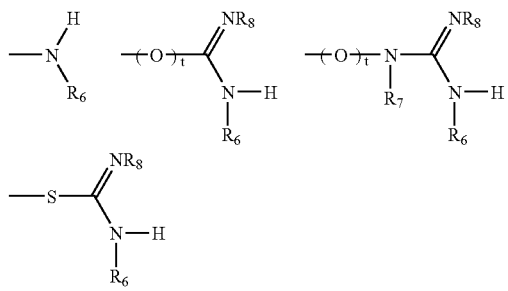

where t=0, 1; $R_6$ and $R_7$ are independently of one another hydrogen or an alkyl group having 1 to 6 C atoms or an alkylene group having 1 to 5 C atoms which forms a ring with $A_2$, or are a hydroxyl, amino, alkylamino, acyl or alkyloxycarbonyl group, where the alkylamino, acyl and alkyloxycarbonyl groups have independently of one another 1 to 6 C atoms, and where $R_8$ is hydrogen or an alkyl group having 1 to 3 C atoms, or is an alkylene group having 1 to 3 C atoms which forms a ring with $R_6$;

(v) Q is either a CH group or N;

(vi) j=0, 1, 2;
  k=0, 1, 2, 3;
  m, n are independently of one another=0, 1, 2, 3, 4, 5, where m+n=3, 4, 5; and where the compound of formula (I) is neither

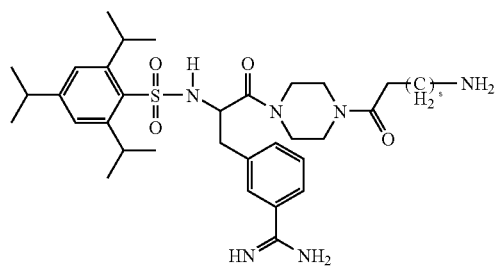

(A1)

with s=0, 2 nor

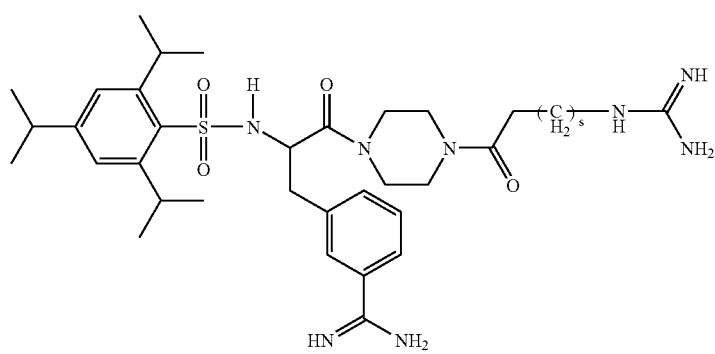

with s=0, 1.

If the abovementioned compounds of the invention are in the form of a salt, then salts with mineral acids and/or salts with suitable organic acids are preferred. It is preferred inter alia for the compounds of the invention to be in the form of hydrochlorides or else of sulfates. Examples of suitable organic acids are formic acid, acetic acid, methylsulfonic acid, succinic acid, malic acid and trifluoroacetic acid. It is preferred inter alia for salts of the compounds of the invention with suitable organic acids to be acetates.

In a preferred embodiment, the compound of the invention has a structure in which at least one of the radicals $X_1$ and $X_2$ has a structure (I'). Within the scope of this embodiment of the non-cyclic imines which are linked to the carbonyl group of the amino acid in the center of (I), preferred compounds are those in which exactly one of the radicals $X_1$ and $X_2$ has a structure (I'). The non-cyclic radical in this case is particularly preferably hydrogen, methyl, ethyl or n-propyl, further preferably methyl or ethyl and particularly preferably methyl. In relation to the substituted cyclic radical, preferred embodiments are those in which m+n is equal to 3 or 4. The radical $R_4$ which is obligatorily present in the radical $R_3$ can generally be chosen as desired within the scope of the definitions made above. Very particularly preferred radicals $R_4$ are those which are unmodified and which are selected from the group consisting of

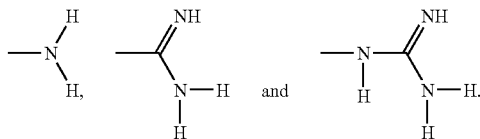

The indices m and n of the ring in (I') can be chosen so that the radical $R_3$ can in principle be located in the 2, 3 or, depending on the ring size, also in the 4 position relative to the nitrogen linked to the carbonyl group of the central amino acid. For example, the 3 or 4 position is preferred, and when m=n=2 the 4 position is particularly preferred.

Within the scope of the embodiment of the non-cyclic imines linked to the carbonyl group of the amino acid in the center of (I), radicals $R_3$ which are further preferred are those in which $A_2$ is absent. Radicals $R_3$ in which the functional group T is either absent or is selected from (A2)

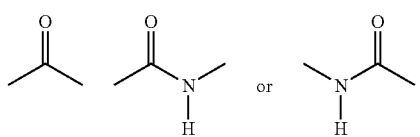

are further preferred. Very particularly preferred embodiments are those in which T is absent. In relation to the group $A_2$, preferred within the scope of the non-cyclic imines linked to the carbonyl group of the amino acid in the center of (I) are alkylene groups having 1, 2, 3, 4 or 5 C atoms, in particular the methylene, ethylene, n-propylene, isopropylene, butylene and pentylene group.

In the case where $A_2$ is an aryl-, heteroaryl- or aralkylene group, mention should be made for example of groups of the structures

where v and w can independently of one another be 0, 1 or 2, and the two alkylene groups may also be positioned in the 1,2 or 1,3 position relative to one another. The 1,4 position is preferred, for example. Both the aryl radical and at least one of the two alkylene groups may be suitably substituted as defined above. If $A_2$ includes a heteroaryl group, this preferably has 1 to 3 heteroatoms.

The ring of (I') can in principle comprise at least one heteroatom, those to be mentioned in this connection as preferred being oxygen, nitrogen or sulfur. If the heteroatom is, for example, nitrogen, this nitrogen may have as further radical for example hydrogen or a linear, branched or cyclic alkyl group having 1 to 10 C atoms, or form a double bond with an adjacent C atom of the ring. In a particularly preferred embodiment, none of the methylene groups in (I') is substituted by a heteroatom.

If the ring of (I') is additionally substituted, preferred additional substituents are, inter alia, carboxyalkyl groups of the general structure —COOR$_2$', it being further preferred for R$_2$' to be an alkyl group having 1, 2 or 3 C atoms and particularly preferably a methyl or ethyl group.

In a preferred embodiment, the compounds of the invention according to (b) have a cyclic imine linked to the carbonyl group of the amino acid in the center of (I), and thus have a structure (I'').

Accordingly, the present invention also relates to a compound as described above, where this compound has the structure (I'')

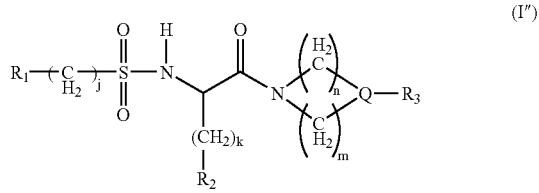

(I'')

The ring in (I'') has in this connection preferably 5, 6 or 7 ring atoms. It is accordingly conceivable for the radical R$_3$ to be located in the 2, 3 or 4 position relative to the imine nitrogen linked to the carbonyl group of the central amino acid. Embodiments which are preferred inter alia are those in which the ring of the cyclic amine has 5 or 6 ring atoms.

A six-membered ring is particularly preferred. In this particularly preferred six-membered ring, the indices m and n can be chosen as desired. Examples of possible combinations are for instance m=0 and n=4, m=1 and n=3, m=2 and n=2, m=3 and n=1, m=4 and n=0. In a very particularly preferred embodiment of the compounds of the invention, m=n=2. The group Q in the structure (I) is thus very particularly preferably located in the 4 position relative to the imine nitrogen linked to the carbonyl group of the central amino acid.

Accordingly, the present invention also relates to a compound as described above, which is characterized in that m=n=2.

In the context of the present invention, the ring of the cyclic imine may be suitably substituted. Among the substituents described above, the COOR$_2$' group is, inter alia, particularly preferred, where R$_2$' is in turn preferably an alkyl group having 1, 2, 3, 4, 5 or 6 C atoms and particularly preferably a methyl group or an ethyl group. If the ring is substituted by a halogen, then fluorine, chlorine and bromine are particularly preferred. The hydroxyl group is likewise a suitable substituent. The ring may further be substituted by two or more identical or different substituents, especially those mentioned as preferred.

At least one of the methylene groups which are indexed with m or n in the ring of (I'') may be substituted by a heteroatom, preferably oxygen, nitrogen or sulfur. If the heteroatom is, for example, nitrogen, this nitrogen may have as further radical for example hydrogen or a linear, branched or cyclic alkyl group having 1 to 10 C atoms, or form a double bond with an adjacent C atom of the ring. The ring in (I'') may very generally comprise at least one double bond, which can be formed either between two heteroatoms, two C atoms or one C atom and one heteroatom. In the context of the present invention, accordingly, rings having at least one double bond and in which the imine nitrogen linked to the carbonyl group of the central amino acid is retained, that is to say is linked by three single bonds to the adjacent atoms, are described.

In a particularly preferred embodiment, none of the methylene groups in (I'') is substituted by a heteroatom. In a further especially preferred embodiment, the methylene groups from which the ring is constructed are not substituted.

Accordingly, the present invention also relates to a compound as described above, where the ring formed by $X_1$ and $X_2$ has the following structure

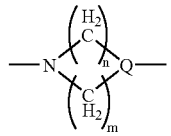

and m, n are independently of one another=0, 1, 2, 3, 4, 5, where m+n=3, 4, 5. Further preferred in this connection are compounds in which m and n are chosen so that a six-membered ring is formed. Accordingly, in this case Q can, as described above, be located in the 2, 3 or 4 position relative to the imine nitrogen, with the 4 position being particularly preferred. Particular preference is further given to m=n=2.

In the context of the present invention, Q is a CH group or nitrogen. The present invention likewise also describes compounds in which this CH group bears a suitable substituent instead of hydrogen. Substituents to be mentioned inter alia as preferred are those with which the methylene groups of the ring can also be substituted.

Accordingly, the present invention also describes a compound as described above, which is characterized in that Q is a nitrogen atom.

Within the scope of this embodiment, the group A$_1$ present where appropriate in the radical R$_3$ can be chosen as desired within the scope of the definitions described above. A particularly preferred group A$_1$ is a methylene or ethylene or propylene group, especially a methylene or ethylene group and is optionally substituted, where as substituents inter alia particularly preferred are alkyl radicals having 1, 2 or 3 C atoms, especially methyl and ethyl, particularly preferably methyl, and/or halogen, especially fluorine, chlorine and bromine, and/or cycloalkyl radicals having preferably 5, 6 or 7 C atoms and/or carboxyalkyl radicals, where the alkyl radical is preferably methyl or ethyl, and the carboxyl group is preferably esterified with a methyl or ethyl group, or is amidated.

In a very particularly preferred embodiment of the compounds of the invention in which Q is a nitrogen atom, the group $A_1$ is absent.

Accordingly, the present invention also describes a compound as described above, which is characterized in that Q is a nitrogen atom and $A_1$ is absent.

Concerning the functional group T which is optionally present in the radical $R_3$ in the context of the present invention, it is possible to choose all of the groups described above. Especially in the case where Q is a nitrogen atom, preferred functional groups T are groups of the structures

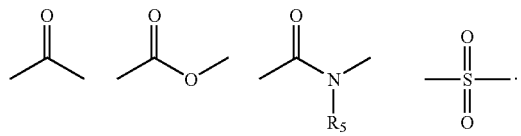

Structures particularly preferred for T groups are

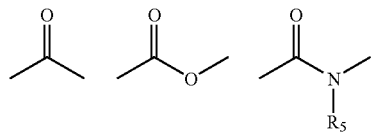

where it is further preferred for $R_5$ to be hydrogen. In further particularly preferred embodiments, T is a group of the structures

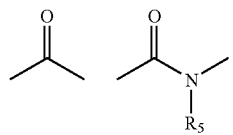

where T is very particularly preferably a functional group of the structure

In this case it is possible for the amide or ester groups to be incorporated in both orientations.

Accordingly the present invention also describes a compound as described above, which is characterized in that Q is a nitrogen atom and T is a functional group of the structure

In relation to the group $A_2$ which is obligatorily present in the radical $R_3$, there are no restrictions within the definitions described above.

Especially in the case where Q is a nitrogen atom and further especially where T is a carbonyl group, alkylene groups having 1 to 6 C atoms are preferred for the group $A_2$, and the methylene, ethylene, propylene, butylene groups are particularly preferred, and the methylene, ethylene and propylene groups are especially preferred.

In the case where $A_2$ is an aryl-, heteroaryl- or aralkylene group, groups of the structures

should be mentioned by way of example, where v and w can independently of one another be 0, 1 or 2, and the two alkylene groups can also be positioned in the 1,2 or 1,3 position relative to one another. The 1,4 position is preferred for example. Both the aryl radical and at least one of the two alkylene groups may be suitably substituted. If $A_2$ includes a heteroaryl group, this preferably has 1 to 3 heteroatoms.

The group $A_2$ can also be suitably substituted as defined above. Substituents in this connection are particularly halogens, preferably fluorine, chlorine or bromine, and/or alkyl radicals having preferably 1, 2 or 3 C atoms such as methyl, ethyl, n-propyl or isopropyl, especially preferably methyl and ethyl, and/or cycloalkyl radicals preferably having 5, 6 or 7 C atoms and/or carboxyalkyl radicals, where the alkyl radical is preferably methyl or ethyl, and the carboxyl group is preferably esterified with a methyl or ethyl group, or is amidated.

In a very particularly preferred embodiment of the present invention, the group $A_2$ is unsubstituted. Accordingly, the present invention describes a compound as described above, which is characterized in that $A_2$ is a methylene, ethylene or propylene group. In particular, the present invention describes a compound as described above, which is characterized in that it has the following structure:

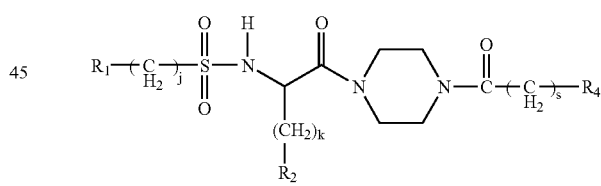

where s=1, 2, 3.

In a likewise preferred embodiment, the present invention describes a compound as described above, which is characterized in that it has as functional group T a group of the structure

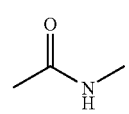

and thus has the following structure:

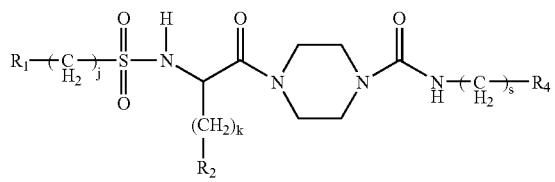

where s=1, 2, 3, preferably s=2.

All the abovementioned structures can be employed as radical $R_4$ obligatorily present in the radical $R_3$. In this connection, t=0 is preferred. Especially preferred in this connection are radicals $R_4$ of the following structures:

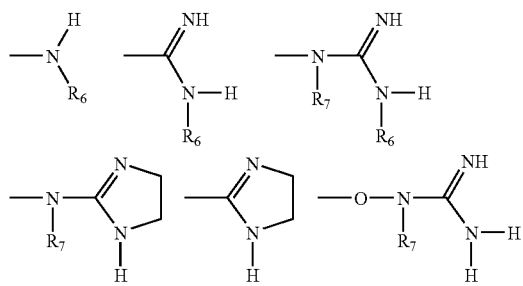

where it is further preferred for $R_6$ and $R_7$ to be equal to hydrogen.

Very particularly preferred radicals $R_4$ are those of the following structures:

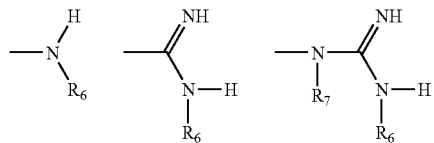

where it is further preferred for $R_6$ and $R_7$ to be equal to hydrogen.

Accordingly, the present invention also relates to a compound as described above, which is characterized in that $R_4$ is selected from the group consisting of

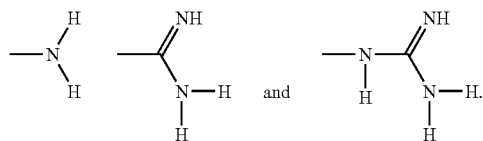

In a likewise preferred embodiment of the present invention, Q is a CH group. The present invention therefore also describes compounds as described above, which are characterized in that Q is a CH group.

Within the scope of this embodiment, the group $A_1$ present where appropriate in the radical $R_3$ can be chosen as desired within the scope of the definitions described above.

A particularly preferred group $A_1$ is a methylene or ethylene or propylene group, especially a methylene or ethylene group and is optionally substituted, where as substituents inter alia particularly preferred are alkyl radicals having 1, 2 or 3 C atoms, especially methyl and ethyl, and/or halogen, especially fluorine, chlorine and bromine, and/or cycloalkyl radicals having preferably 5, 6 or 7 C atoms and/or carboxyalkyl radicals, where the alkyl radical is preferably methyl or ethyl, and the carboxyl group is preferably esterified with a methyl or ethyl group, or is amidated.

In a very particularly preferred embodiment of the compounds of the invention in which Q is a CH group, the group $A_1$ is absent.

Accordingly, the present invention also describes a compound as described above, which is characterized in that Q is a CH group and $A_1$ is absent.

Concerning the functional group T which is optionally present in the radical $R_3$ in the context of the present invention, it is possible to choose all of the groups described above. Especially in the case where Q is a CH group, preferred functional groups T are groups of the structures

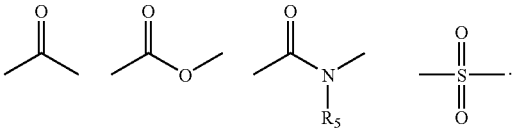

Structures particularly preferred for T groups are

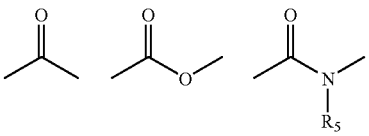

where it is further preferred for $R_5$ to be hydrogen. In further particularly preferred embodiments, T is a group of the structures

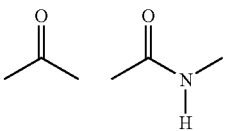

where T is very particularly preferably a functional group of the structure

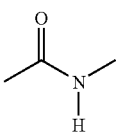

In this case it is possible for the amide or ester groups to be incorporated in both orientations.

Accordingly, the present invention also describes a compound as described above, which is characterized in that Q is a CH group and T is a functional group of the structure

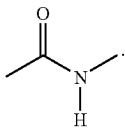

In the case where Q is a CH group and T is one of the functional groups mentioned as preferred, the group $A_1$ is absent in a particularly preferred embodiment of the present invention.

The present invention therefore also describes a compound as described above, which has the following structure:

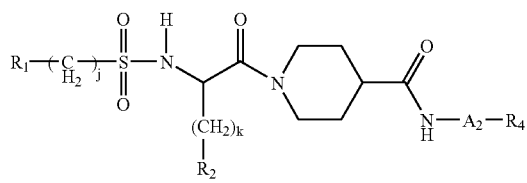

Besides the 4 position of the radical $R_3$ which is explicitly described in the above structural formula, the 2 or 3 position are likewise possible, with preference for the 4 position.

In a likewise preferred embodiment of the present invention, both group $A_1$ and the functional group T are absent.

The present invention therefore also describes a compound as described above, which has the following structure:

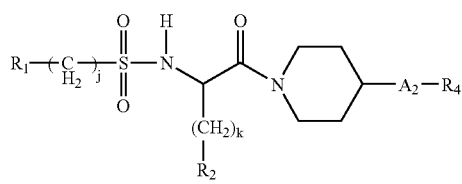

Besides the 4 position of the radical $R_3$ which is explicitly described in the above structural formula, the 2 or 3 position are likewise possible, with preference for the 4 position.

In relation to the group $A_2$ which is obligatorily present in the radical $R_3$, there are, as already discussed above, no restrictions within the definitions described above.

Especially in the case where Q is a CH group and further especially when either T is a group of the structure

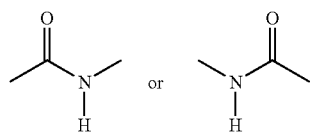

or is absent, alkylene groups having 1 to 6 C atoms are preferred for the group $A_2$, especially the methylene, ethylene, propylene, butylene groups, further especially the methylene, ethylene and propylene groups and very especially the ethylene group.

In the case where $A_2$ is an aryl, heteroaryl or aralkylene group, groups of the structures

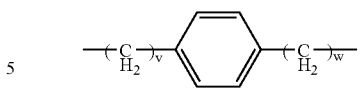

should be mentioned by way of example, where v and w can independently of one another be 0, 1 or 2, and the two alkylene groups can also be positioned in the 1,2 or 1,3 position relative to one another. The 1,4 position is preferred for example. Both the aryl radical and at least one of the two alkylene groups may be suitably substituted. If $A_2$ includes a heteroaryl group, this preferably has 1 to 3 heteroatoms.

The group $A_2$ can also be suitably substituted as defined above. Substituents in this connection are particularly halogens, preferably fluorine, chlorine or bromine, and/or alkyl radicals having preferably 1, 2 or 3 C atoms such as methyl, ethyl, n-propyl or isopropyl, especially preferably methyl and ethyl, and/or cycloalkyl radicals preferably having 5, 6 or 7 C atoms and/or carboxyalkyl radicals, where the alkyl radical is preferably methyl or ethyl, and the carboxyl group is preferably esterified with a methyl or ethyl group, or is amidated.

In a very particularly preferred embodiment of the present invention, the group $A_2$ is unsubstituted.

Accordingly, the present invention also describes compounds as described above, which are characterized in that they have the following structure:

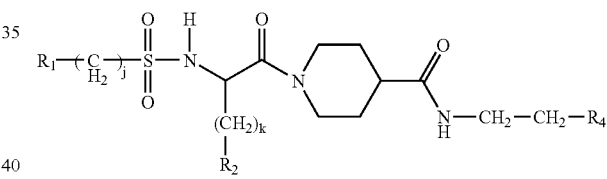

Besides the 4 position of the radical $R_3$ which is explicitly described in the above structural formulae, the 2 or the 3 position are likewise possible, with preference for the 4 position.

The present invention therefore likewise also describes compounds as described above, which are characterized in that they have the following structures:

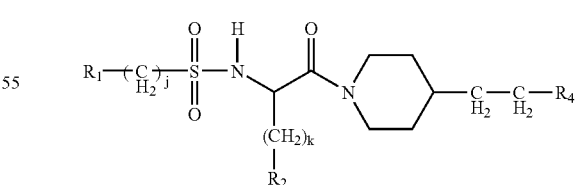

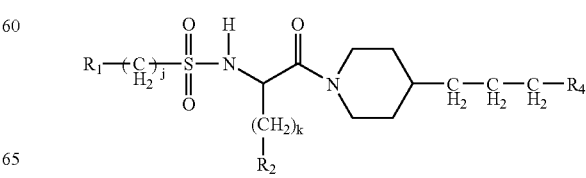

-continued

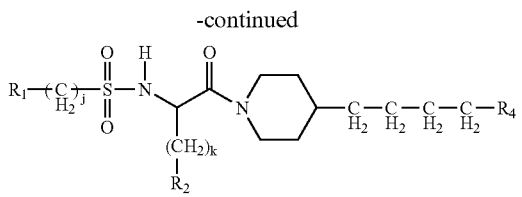

Besides the 4 position of the radical $R_3$ explicitly described in the above structural formulae, the 2 or the 3 position are also possible, with preference for the 4 position.

All the abovementioned structures can be employed as radical $R_4$ obligatorily present in the radical $R_3$. In this connection, t=0 is preferred. Especially preferred in this connection are radicals $R_4$ of the following structures:

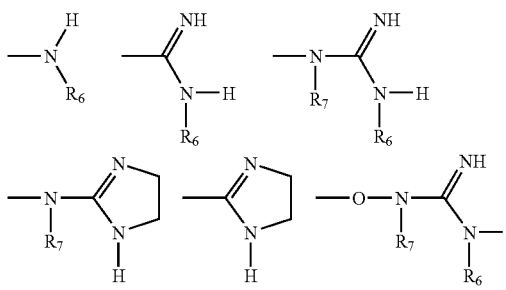

where it is further preferred for $R_6$ and $R_7$ to be equal to hydrogen.

Very particularly preferred radicals $R_4$ are those of the following structures:

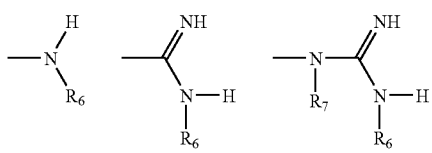

where it is further preferred for $R_6$ and $R_7$ to be equal to hydrogen.

Accordingly, the present invention also relates to a compound as described above, which is characterized in that $R_4$ is selected from the group consisting of

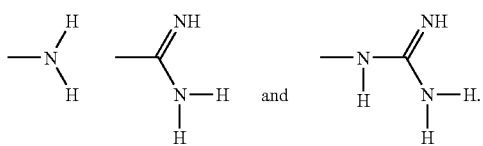

The radical $R_4$ present in the radical $R_3$ is in the context of the present invention particularly preferably of the structure

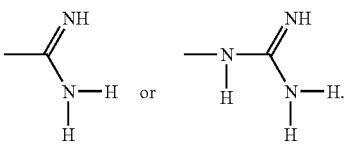

In relation to the radical $R_2$, generally all the radicals falling under the definition (ii) are possible. Accordingly, conceivable aryl groups are for example the phenyl group or the naphthyl group, where at least one of the C atoms of this aryl group can be replaced by a heteroatom selected from the group consisting of S, N and O. A phenyl radical is particularly preferred as radical $R_2$. Thienyl and pyridyl are preferred as an aryl radical comprising at least one heteroatom.

Accordingly, the present invention relates to a compound as described above, which is characterized in that $R_2$ is an at least monosubstituted phenyl radical, thienyl radical or pyridyl radical.

In a particularly preferred embodiment, $R_2$ is an at least monosubstituted phenyl radical.

The aryl radical, particularly preferably the phenyl radical, $R_2$ has at least one substituent $R_4$ as defined above, where one of the structures

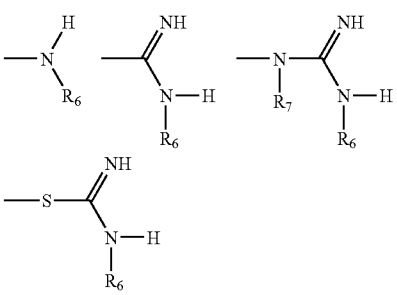

is preferred.

A particularly preferred substituent $R_4$ in this connection is one selected from the group consisting of

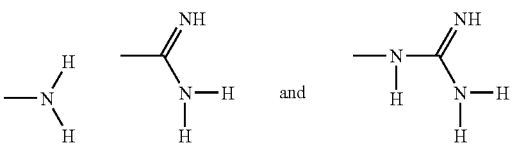

A substituent of the structure

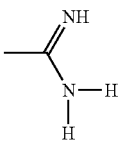

is very particularly preferred as radical $R_4$. The substituent $R_4$ can generally be positioned at all positions of the aryl radical. In relation to the particularly preferred phenyl radical, accordingly the 2, 3 or 4 position of the radical $R_4$ is possible, where the 3 position of the radical $R_4$ on the phenyl radical is particularly preferred.

Besides the radical $R_4$, the aryl radical may further have at least one further substituent. In a particularly preferred embodiment, the aryl radical has a single substituent.

The alkylene group to which the radical $R_2$ on the alpha-C atom of the central amino acid in (I) is linked generally has 0 to 3 C atoms. This alkylene group preferably has 1, 2 or 3 C atoms, particularly preferably 1 or 2 C atoms and very particularly preferably 1 C atom.

Accordingly, the present invention describes a compound as described above, which is characterized in that it has the following structure:

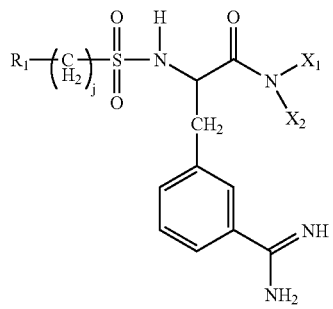

The structure shown above may generally have both the D and the L configuration at the α-C atom of the 3-amidinophenylalanine. In the context of the present invention, the L configuration is particularly preferred. The compounds (1) of the invention may very generally have either the L or the D configuration or be the racemate in relation to the central alpha-amino acid.

Accordingly, the present invention also relates to a compound as described above, which is characterized in that k=1 and $R_2$ is a phenyl radical meta-substituted by an amidino group, where the 3-amidinophenylalanine resulting thereby is in the L configuration.

It is possible in principle for the compounds (I) to have, when a further asymmetric C atom is present besides the abovementioned asymmetric C atom, or another center of asymmetry is present, both the L and the D configuration or S or R configuration. It is likewise possible for the compound (I) to be in the form of a racemate. Mixtures of L and D configurations or S and R configurations are furthermore possible, where the proportion of molecules with the D configuration or the proportion of molecules with L configuration or, respectively, the proportion of molecules with the S configuration or the proportion of molecules with the R configuration, predominates.

It is possible in general for every radical $R_1$ described in the above definition (i) to be present as radical $R_1$.

If the radical $R_1$ is substituted for example by at least one halogen, in this case fluorine, chlorine and/or bromine are preferred.

If the radical $R_1$ is substituted for example by at least one esterified carboxyl group, methyl esters and/or ethyl esters are preferred.

If the radical $R_1$ is substituted for example by at least one amino group, this amino group may be acylated, in which case the acetyl group is particularly preferred.

Particular preference is given for example to mono-, bi- or tricyclic aryl radicals and heteroaryl radicals in which optionally at least one double bond is hydrogenated and/or which comprise at least one heteroatom selected from O, S and N, it also being possible for a heteroaryl radical $R_1$ to comprise two or more identical or different heteroatoms. Examples of preferred aryl radicals are for instance phenyl, naphthyl, anthracyl or phenanthryl. These aryl radicals may optionally be in reduced or/and oxidized form. In relation to the naphthyl radical, for example, a 1,2-dihydronaphthyl, a 1,4,-dihydronaphthyl or else a 1,2,3,4-tetrahydronaphthyl radical is possible. In oxidized form, the naphthyl radical may for example be in the form of a 1,4-naphthoquinoyl radical. The anthraquinoyl radical may in oxidized form be for example in the form of a 1,4- or 9,10-anthraquinoyl radical or 1,4- or 9,10-anthrahydroquinoyl radical, and the phenanthryl radical for example in the form of a phenanthrenequinoyl radical.

Examples of heteroaryl radicals are for instance pyrrolyl, furanyl, thiophenyl, pyridyl, pyrimidyl, pyrazyl, triazyl, imidazolyl, thiazolyl, oxazolyl, indolyl, purinyl, pyronyl, pyridonyl, quinolyl, isoquinolyl. Also included likewise are radicals $R_1$ such as indenyl or tetrahydroindenyl.

It is further possible for the radical $R_1$ to be suitably substituted, preferred substituents being for example linear, branched or cyclic alkyl radicals having 1 to 10 C atoms.

Linear or branched alkyl radicals having 1, 2, 3, or 4 C atoms are particularly preferred. Examples of particularly preferred substituents are isopropyl and tert-butyl. Cyclic alkyl radicals are likewise preferred as substituents, with cyclic alkyl radicals having 5, 6 or 7 C atoms and, in particular, 6 C atoms being particularly preferred. Mention should likewise be made of aryl or heteroaryl groups as substituents, it being possible for the heteroaryl groups to comprise one heteroatom selected from N, S and O, and to comprise two or more identical or different heteroatoms. The substituents of the radical $R_1$ may in turn themselves be suitably substituted.

Both heteroaryl and aryl radicals and alkyl radicals may in this connection be linked by a sulfur bridging atom or an oxygen bridging atom or via an alkylene chain having 1-3 C atoms to the radical $R_1$. Accordingly, the radical $R_1$ may be substituted for example by an alkyloxy, alkylthio, aryloxy, arylthio, heteroaryloxy or heteroarylthio group.

Examples of substituted radicals $R_1$ are for instance

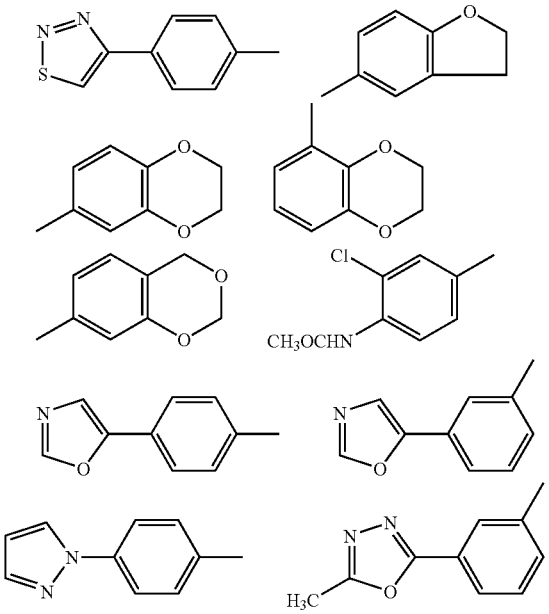

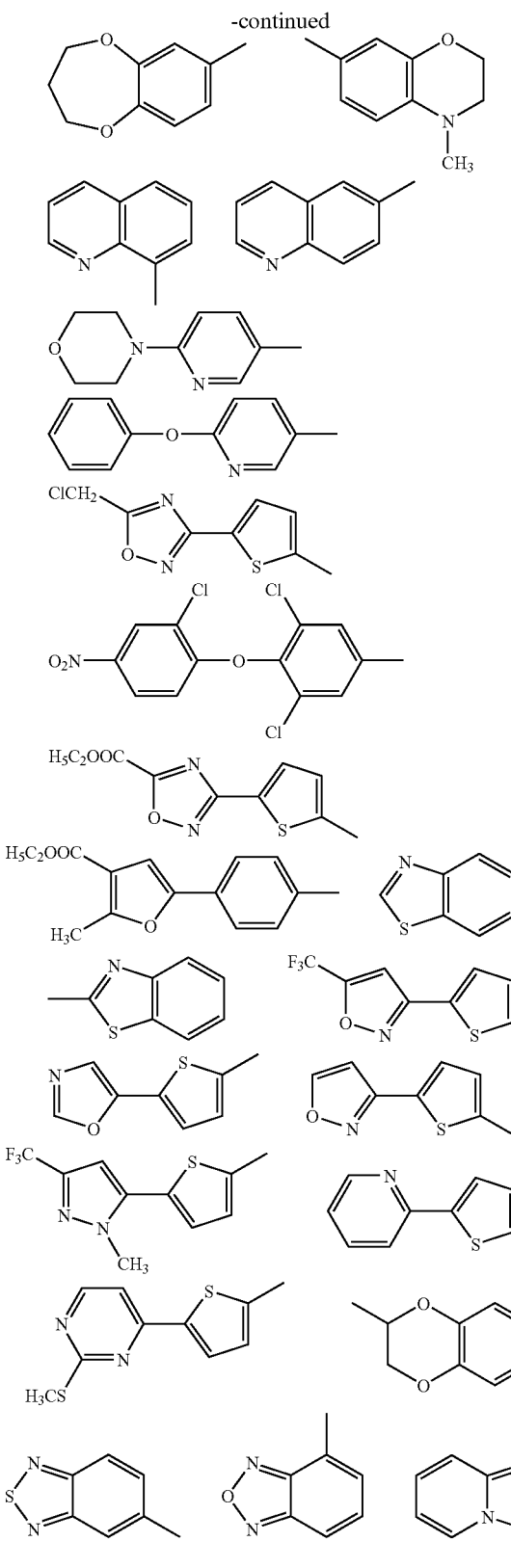

one, two or three substituents. If the aryl radical has for example three substituents, then alkyl radicals having 1, 2 or 3 C atoms are preferred inter alia Alkyl radicals having 2 or 3 C atoms are particularly preferred, especially preferably alkyl radicals having 3 C atoms and especially particularly preferably isopropyl. Especially preferred in this connection is, for example, the 2,4,6-triisopropylphenyl radical.

If the aryl radical has for example one substituent, then the tert-butyl radical is preferred inter alia.

In a further suitable embodiment, the radical $R_1$ is an aryl radical, preferably a phenyl radical, which is substituted by a further aryl radical or heteroaryl radical via an oxygen bridging atom or via an alkylene chain having 1-3 C atoms in turn having an aryl, heteroaryl or alkyl radical. It is possible in this case for the aryl or heteroaryl radical, for example a pyridine, to be unsubstituted or likewise substituted at a suitable position, in ortho, meta or para position, for example by at least one alkyl group such as, for example, a methyl group and/or by at least one halogen atom, preferably by one chlorine atom or two chlorine atoms or one or two fluorine atoms and/or by at least one trihalomethyl group, preferably by one or two trifluoromethyl group(s) and/or by by at least one alkoxy group, preferably a methoxy group.

Examples of such radicals $R_1$ are for instance

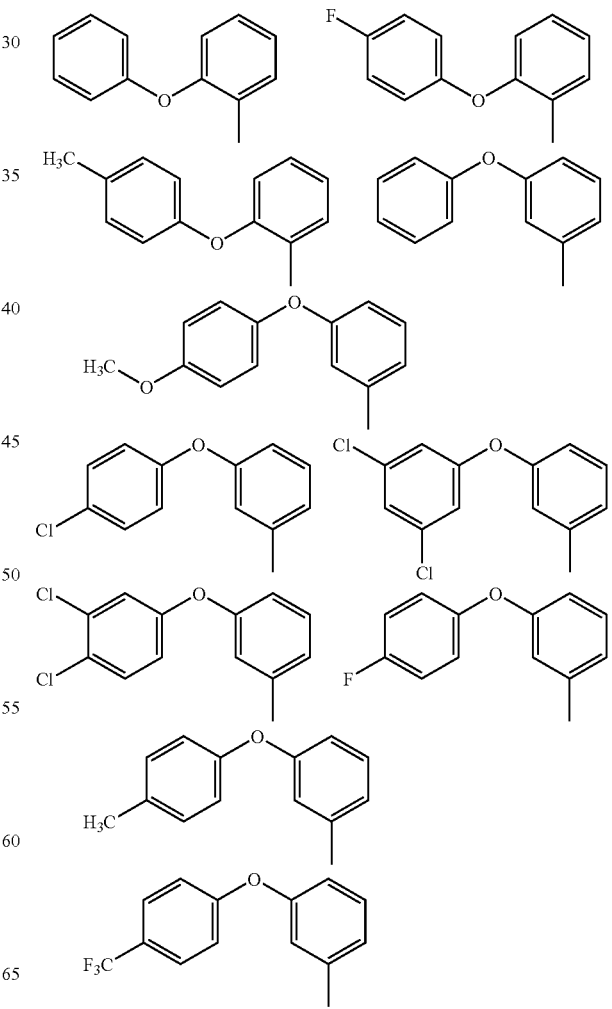

An aryl radical which is preferably present may in principle also have more than one substituent. Particularly preferred embodiments are those in which the aryl radical has no, -continued

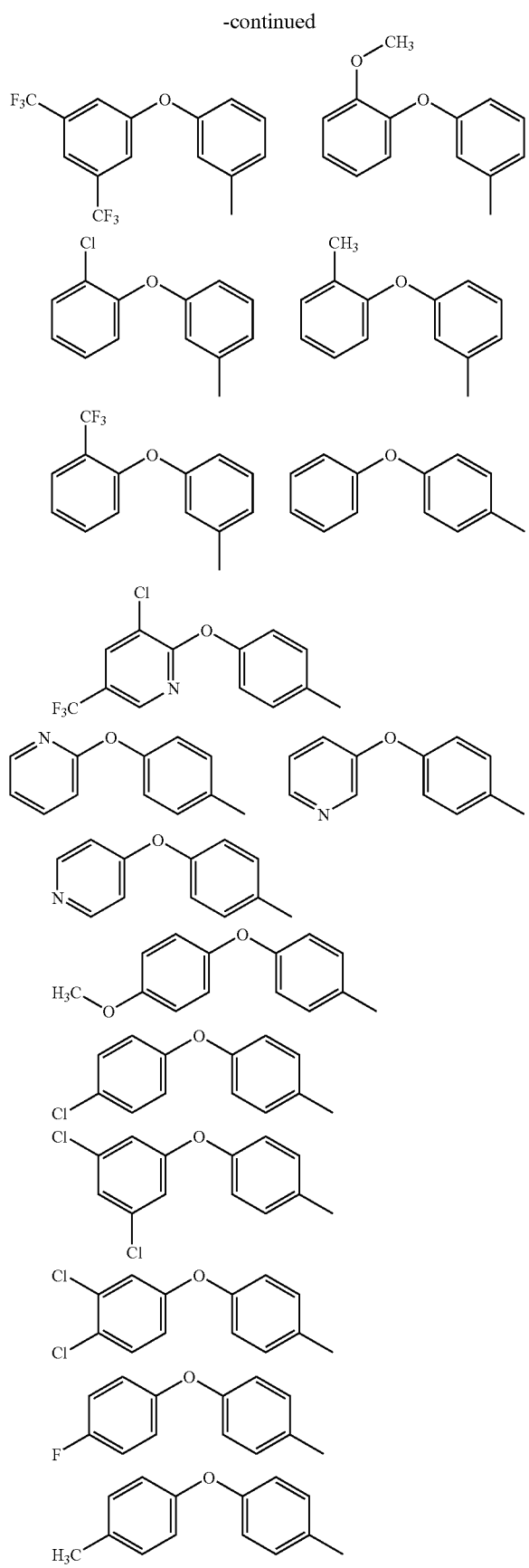

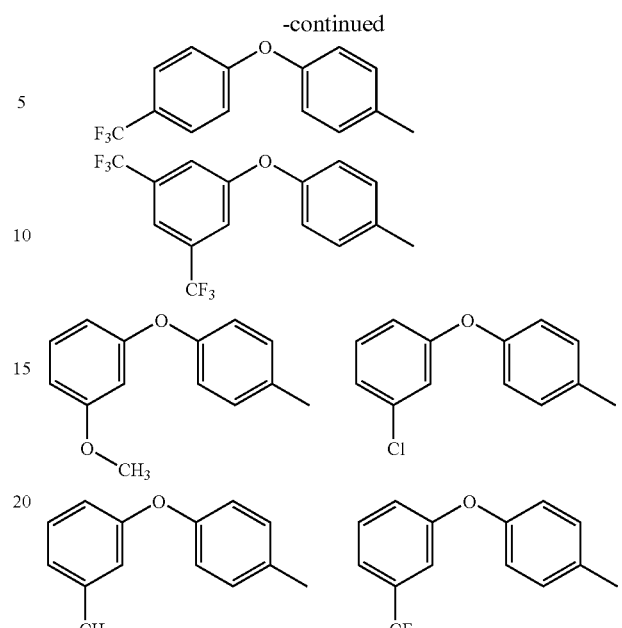

where the oxygen connecting the two aryls may be replaced by an alkylene chain having 1-3 C atoms.

In a particularly preferred embodiment, the radical $R_1$ is selected from tert-butylphenyl, cyclohexylphenyl, 5,6,7,8-tetrahydronaphthyl, naphthyl, anthracyl, anthraquinoyl and anthrahydroquinoyl, pyridyloxyphenyl, phenyloxypyridyl, pyridylalkylphenyl having a $C_1$-$C_3$-alkyl.

The alkylene group which links the radical $R_1$ and the sulfonyl group generally has no, one or two C atoms. It preferably has no or one C atom, and especially preferably has no C atom and is thus absent.

An alternative embodiment of the invention are compounds of the formula I"

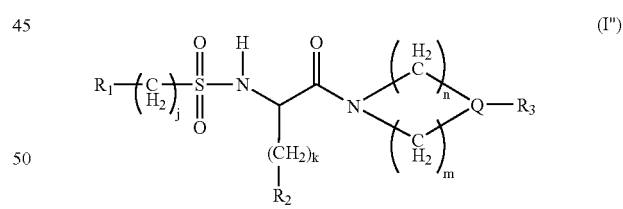

(I")

where $R_1$, $R_2$, Q, j and k are defined as described above, m=n=2, and $R_3$ is an aryl or heteroaryl radical, and where the aryl radical is preferably a benzyl or a phenoxy radical, and the heteroaryl radical is preferably selected from a pyridinylmethylene, pyridinyloxo, pyrimidinyloxo, pyrazinyloxo, pyridinylthio radical and where the aryl or heteroaryl radical is unsubstituted or substituted by at least one halogen, preferably fluorine or chlorine, at least one alkoxy radical, preferably methoxy radical, and/or at least one trifluoromethyl radical.

In a further preferred embodiment, the radical $R_3$ is a guanidinooxyalkyl radical.

Examples of such compounds are compounds in which the structural unit

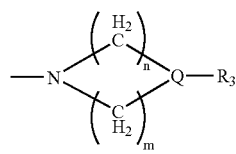

in formula I" is replaced by

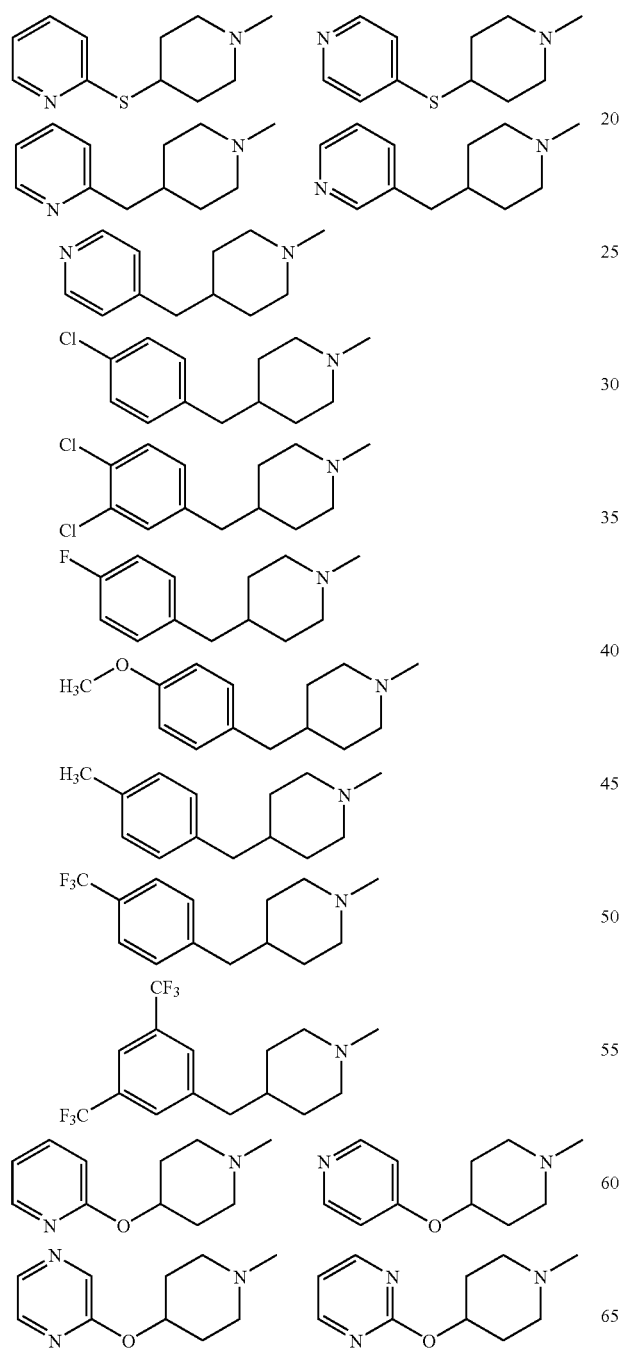

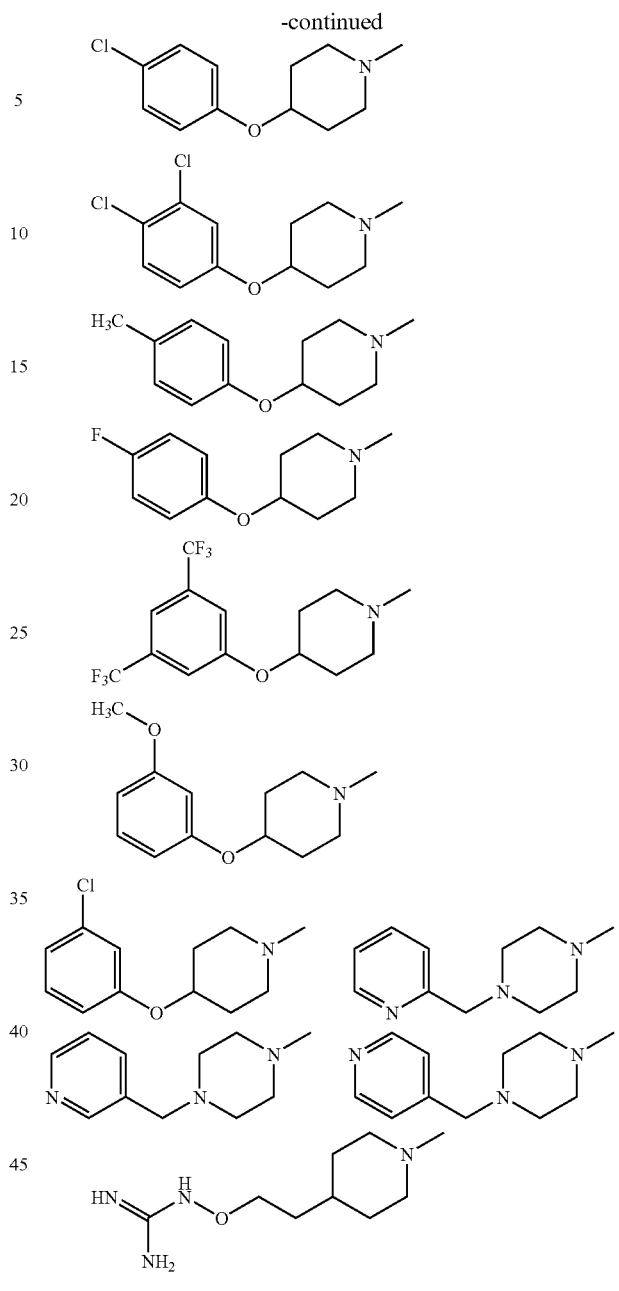

which are commercially available from Array Biopharma, Bolder Colo., U.S.A.

Likewise included are compounds in which an amino acid, preferably glycine, is incorporated between the sulfonyl group and the 3-amidinophenylalanine group of the formula I.

The compounds described above can generally be prepared by all suitable processes. The compounds of the invention are preferably prepared by processes in which a sulfonyl chloride is reacted in a first step with an amino acid or an amino acid derivative.

Accordingly, the present invention relates to a process for preparing a compound as described above, which comprises the following step (S1):

(S1) reaction of a compound of the general structure (E1')

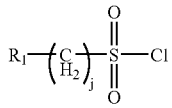
(E1')

with a compound of the general structure (E1")

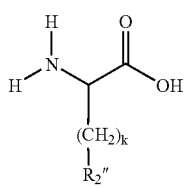
(E1")

to obtain a compound of the general structure (ZP1)

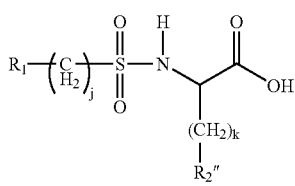
(ZP1)

where $R_2''$ is the aryl radical $R_2$ substituted either by $R_4$ or by $R_4$ protected with a suitable protective group, or by a substituent which is a precursor of $R_4$.

If the aryl radical $R_2$ is substituted for example preferably by an amidino group $R_4$, then the substituent which represents a precursor of the amidino group is for example a cyano group which can be converted in one, preferably two or more suitable process stages by reaction with hydroxylamine and subsequent hydrogenation into an amidino group. This amidino group can subsequently in turn be protected with a suitable protective group which can be removed again in a suitable process step.

If compounds of the invention of the general structure (I") in which the group Q is equal to nitrogen, and the alkylene group $A_1$ is absent, are prepared, then preferred preparation processes are those wherein a compound of the structure (ZP1) is initially reacted in a step (S2') with a cyclic compound of the general structure (E2').

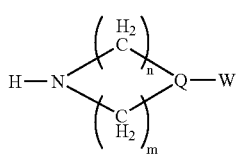
(E2')

where W is a suitable protective group. In this case, a compound of the general structure (ZP2')

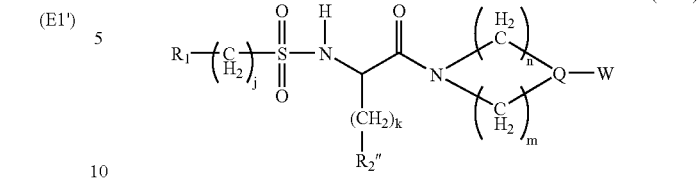
(ZP2')

is obtained, from which the protective group W is preferably eliminated in a subsequent step (S3'). In a next step (S4'), the compound obtained in (S3') is reacted with a compound of the general structure (E2")

(E2")

resulting in a compound of the general structure (P1)

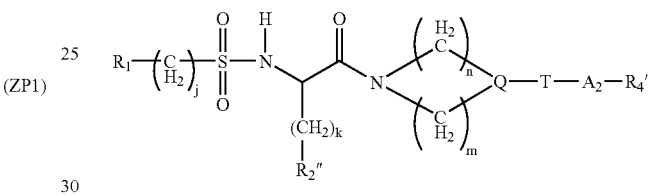

where $R_4'$ is either $R_4$ or $R_4$ protected with a suitable protective group, or a precursor of $R_4$. If $R_4'$ is a radical $R_4$ protected with a protective group, then the protective group is preferably removed after step (S4').

It is then possible according to the invention for an amino group to be present as radical $R_4$. It is then possible to build up from this group a guanidino group in a next step by a process known to the skilled worker, for example by reaction with pyrazolecarboxamidine.

A likewise preferred process for preparing compound (I") in which the group Q is equal to nitrogen, and the alkylene group $A_1$ is absent, comprises a step (S2') in which a compound of the general structure (E2''')

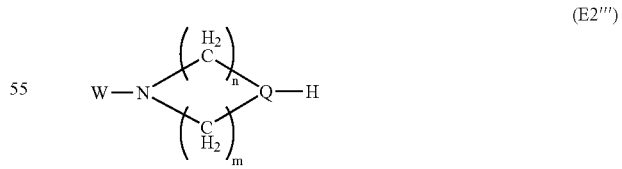
(E2''')

where W is a suitable protective group, is reacted with a compound of the general structure (E2")

(E2")

resulting in a compound of the general structure (ZP2")

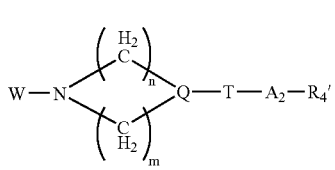
(ZP2'')

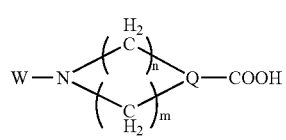
(E3')

in which $R_4'$ is either $R_4$ or $R_4$ protected with a suitable protective group, or a precursor of $R_4$. In this process therefore firstly the C-terminal radical of the central amino acid in (I) is built up. In a next step (S3'), preferably the protective group W is eliminated, and in a next step (S4') the compound obtained in (S3') is reacted with a compound of the general structure (ZP1) to result in a compound of the general structure (P1). If the radical R in this case is an amino group, then a guanidino group can be built up therefrom in this case too, as described above.

If compounds of the invention of the general structure (I'') in which the group Q is equal to CH are prepared, then preferred preparation processes are those which start from compounds (ZP1) which are reacted in a step (S2'') with a compound of the general structure (E3)

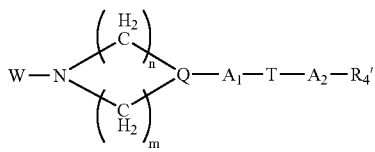
(E3)

where $R_4'$ is either $R_4$ or $R_4$ protected with a suitable protective group, or a precursor of $R_4$. This preferred reaction results in a compound of the general structure (P2)

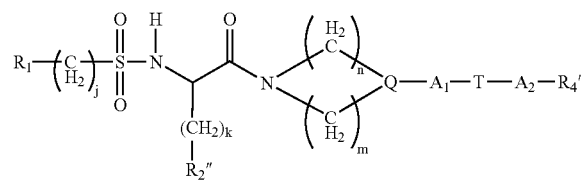
(P2)

If $R_4'$ is a radical $R_4$ protected with a protective group, then the protective group is preferably removed after step (S2''). It is then possible according to the invention for an amino group to be present as radical $R_4$. It is then possible to build up from this group a guanidino group in a next step by a process known to the skilled worker, for example by reaction with pyrazolecarboxamidine.

If compounds of the invention of the general structure (I'') in which T is equal to —(C'—O)—NH—, Q is equal to CH, and $A_1$ is absent, are prepared, then preferred preparation processes are those in which firstly, in a step (S2'''), compounds of the general structure (E3')

are reacted with a compound of the general structure (E3'')

$H_2N-A_2-R_4'$ (P2)

resulting in a compound of the general structure (ZP3)

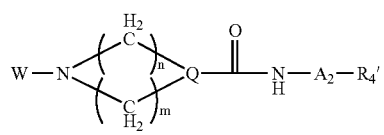
(ZP3)

The radical $R_4'$ has the meaning described in the further preparation processes described above. W is a suitable protective group in this case too. In a next step, the protective group W is removed by a suitable process preferably in a step (S3'''). This is preferably followed by a step (S4''') in which the compound obtained in (S3''') is reacted with a compound (ZP1), resulting in a compound of the general structure (P3)

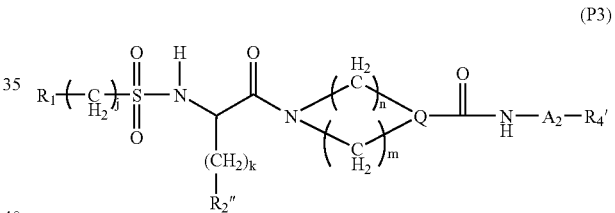
(P3)

If $R_4'$ is a radical $R_4$ protected with a protective group, the protective group is preferably removed after step (S2'''). It is then possible according to the invention for an amino group to be present as radical $R_4$. It is then possible to build up from this group a guanidino group in a next step by a process known to the skilled worker, for example by reaction with pyrazolecarboxamidine.

In a preferred embodiment of this last-described process variant, it is possible to employ as compound of the general structure (E3'') for example a compound which has as radical $R_4'$ a precursor of a radical $R_4$ of the invention, this precursor being a —CN group. In one or more suitable steps, this —CN group is built up to an amidino group further preferably by a process known to the skilled worker, for example by reaction with a hydroxylamine, subsequent reaction with acetic anhydride and following hydrogenation. In another embodiment of the process of the invention, the hydroxyamidino derivative can be converted directly by hydrogenation into an amidine derivative, in which case the amidino group is if appropriate protected intermediately with a suitable protective group. The reaction with hydroxylamine very particularly preferably takes place after step (S2''') and before step (S3'''). It is further particularly preferred for the reaction with acetic anhydride likewise to take place before step (S3'''). Hydrogenation to give the amidino group preferably takes place after step (S4''').

It is very particularly preferred for the final purification of the compounds prepared in this way to take place by preparative, reversed-phase HPLC or by crystallization from a suitable solvent or solvent mixture or by countercurrent distribution.

Besides the compounds described as above per se and processes for their preparation, the present invention also relates to a medicament which comprises one of the compounds indicated above.

Accordingly, the present invention also relates to a medicament comprising at least one compound (I) or a salt of this compound and, where appropriate, pharmaceutically suitable excipients and/or additives.

The present invention likewise describes a compound (I) for use as medicament, where the medicament comprises where appropriate in addition pharmaceutically suitable excipients and/or additives.

Suitable excipients and/or additives which serve, for example, to stabilize and/or preserve the medicament are disclosed for example in H. Sucker et al., Pharmazeutische Technologie, 2nd edition, Georg Thieme Verlag, Stuttgart (1991), the disclosure in this regard being included by reference in the context of the present invention. The pharmaceutically suitable excipients and/or additives include for example physiologically saline solutions, Ringer's dextrose, Ringer's lactate, demineralized water, stabilizers, antioxidants, complexing agents, antimicrobial compounds, proteinase inhibitors and/or inert gases.

The compounds (I) of the invention can generally be employed in any form as medicaments. The medicament is employed in possible embodiments of the invention for example in the form of a tablet, of a coated tablet, of a capsule, of a pellet, suppository, of a solution, in particular of a solution for injection or infusion, of eye drops, nose and ear drops, of a syrup, of a capsule, of an emulsion or suspension, of a pessary, stick, aerosol, dusting powder, of a paste, cream or ointment.

The present invention therefore also relates to a medicament as described above, which is characterized in that it is employed in the form of a tablet, of a coated tablet, of a capsule, of a pellet, of a suppository, of a solution, in particular of a solution for injection or infusion, of eye drops, nose drops or ear drops, of a syrup, of an emulsion or suspension, of a pessary, of a stick, of an aerosol, of a dusting powder, of a paste, of a cream or of an ointment.

The present invention therefore likewise also describes a compound (I) for use as medicament, where the medicament is employed in the form of a tablet, of a coated tablet, of a capsule, of a pellet, of a suppository, of a solution, in particular of a solution for injection or infusion, of eye drops, nose drops or ear drops, of a syrup, of an emulsion or suspension, of a pessary, of a stick, of an aerosol, of a dusting powder, of a paste, of a cream or of an ointment.

In a particularly preferred embodiment of the present invention, the abovementioned compounds (I) and/or their salts or the abovementioned medicaments comprising these compounds (I) and/or their salts and, where appropriate, at least one pharmaceutically suitable excipient and/or additive are employed for the diagnosis and/or therapy of a tumor. Prophylaxis of a tumor is likewise also possible additionally or alternatively, it being possible to use the compounds in particular for preventing and/or reducing the metastasis of tumors.

A compound (I) of the invention or its salt or a medicament as described above can very generally furthermore be employed for example in parenteral use form, especially in intraarterial, intravenous, intramuscular or subcutaneous form, in enteral use form, especially for oral or rectal use, or in topical use form, especially as dermatological agent. Intravenous or subcutaneous uses are preferred.

These use forms are particularly suitable for the diagnosis and/or therapy and/or prophylaxis of a tumor.

The present invention therefore also relates to the use of a compound (I) or of a salt of this compound or of a medicament as described above for the diagnosis, therapy or prophylaxis of a tumor and for preventing and/or reducing the metastasis of a tumor, especially in oral, subcutaneous, intravenous or transdermal form.

The present invention likewise describes the use of a compound (I) or of a salt of this compound for producing a medicament for the diagnosis, therapy or prophylaxis of a tumor and for preventing and/or reducing the metastasis of a tumor.

The present invention further describes this use for producing a medicament for oral, subcutaneous, intravenous or transdermal use.

In a particularly preferred embodiment of the present invention, a compound (I) of the invention is employed for reducing tumor metastases.

Accordingly, the present invention relates to the use described above of the compound (I) or of a salt of this compound or of a medicament as described above, where the formation of tumor metastases is reduced.

The present invention likewise describes a process as described above for producing a medicament for reducing the formation of tumor metastases.

The present invention therefore likewise relates in particular to the use of a compound (I) or of a salt of this compound or of a medicament comprising the compound (I) or a salt of this compound for inhibiting matriptase.

The present invention relates in particular also to the use of a compound (1) or of a salt of this compound or of a medicament comprising the compound (I) or a salt of this compound for inhibiting matriptase, where the matriptase is MT-SP1.

The present invention accordingly also describes a process for producing a medicament comprising a compound (I) or a salt of this compound for inhibiting matriptase.

The present invention likewise also describes a process for producing a medicament comprising a compound (I) or a salt of this compound for inhibiting matriptase, where the matriptase is MT-SP1.

The compounds described above may also be in the form of prodrugs, e.g. through modification of the amidino group with a hydroxyl or a $C_1$-$C_6$-alkyloxycarbonyl group, which are converted into the species having inhibitory activity only after uptake in the body, spontaneously and/or by one or more endogenous enzymes, it thus being possible to improve the bioavailability and pharmacokinetic properties of the compounds.

The invention is explained in more detail in the following examples and figures.

EXAMPLES

Methods

Figure 1:
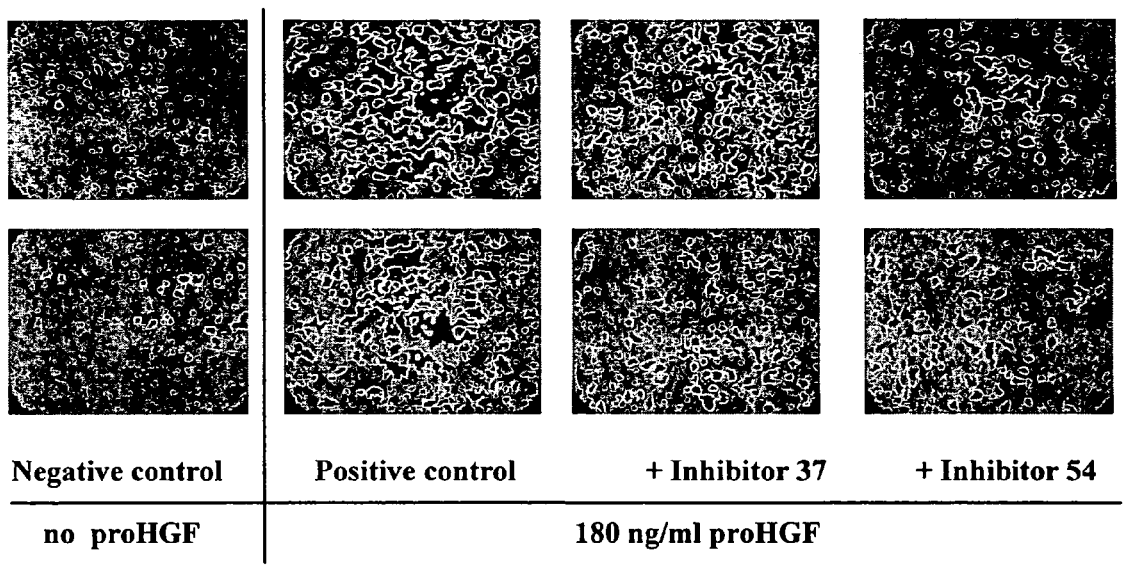
FIG. 1 shows the inhibition of the invasive growth by the matriptase inhibitors 37 and 54 from Example 9.

Analytical HPLC: Shimadzu LC-10A system, column: Phenomenex Luna $C_{18}$, 5 µm, 100 Å (250×4.6 mm) solvent A: 0.1% TFA in water, B: 0.1% TFA in ACN, gradient: 10% B to 70% B in 60 min, 1 ml/min flow rate, detection at 220 or 215 nm.

Preparative HPLC: Shimadzu LC-8A system, column: Phenomenex Luna $C_{18}$, 5 µm, 100 Å (250×30 mm) solvent A: 0.1% TFA in water, B: 0.1% TFA in ACN, gradient: 10% B to 55% B in 120 min, 10 ml/min flow rate, detection at 220 nm.

Mass spectroscopy: The mass spectra were measured on a Kompact probe from Kratos (Manchester, England) with a time of flight measuring detector and α-cyano-hydroxycinnamic acid as matrix, or on an ESI-MS LCQ from Finnigan (Bremen, Germany).

Abbreviations Used
- Ac acetyl
- AcOH acetic acid
- ACN acetonitrile
- β-Ala β-alanine
- Boc tert-butyloxycarbonyl
- DAE 1,2-diaminoethane
- DCM dichloromethane
- DIEA diisopropylethylamine
- DMF N,N-dimethylformamide
- IBCC isobutyl chlorocarbonate
- iNip isonipecotic acid
- $K_i$ inhibition constant
- NMM N-methylmorpholine
- Phe(3-AcOxam) 3-(acetyloxyamidino)phenylalanine
- Phe(3-Am) 3-amidinophenylalanine
- Phe(3-CN) 3-(cyanophenyl)alanine
- Phe(3-Oxam) 3-(oxamidino)phenylalanine
- PyBop benzotriazol-1-yl-N-oxytris(pyrrolidino)phosphonium hexafluoro-phosphate
- Pzd piperazide
- RT room temperature
- TFA trifluoroacetic acid
- THF tetrahydrofuran
- Tips 2,4,6-(triisopropyl)phenylsulfonyl
- Z benzyloxycarbonyl

Example 1

Synthesis of anthracenesulfonyl-Phe(3-Am)-Pzd-β-Ala×2 TFA (Compound 10 from Table 1)

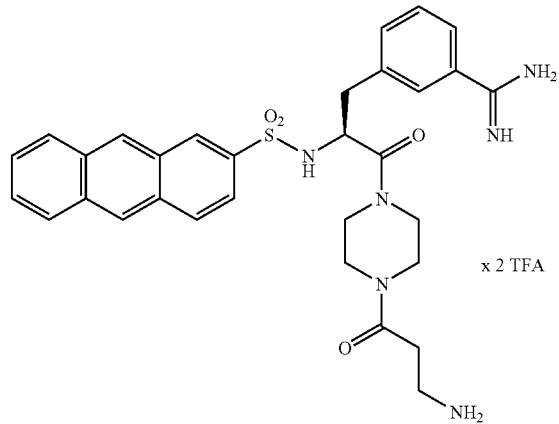

1a) Boc-Pzd-βAla-Z 2 g (8.96 mmol) of Z-βAla-OH were dissolved in 20 ml of THF and, at −15° C., 0.99 ml (8.96 mmol) of NMM and 1.17 ml (8.96 mmol) of IBCC were added. The mixture was stirred at −15° C. for 10 min and then 1.67 g (8.96 mmol) of Boc piperazine (Fluka) and additionally 400 µl (3.6 mmol) of NMM were added. The mixture was stirred at −15° C. for a further hour and further stirred at room temperature overnight. Subsequently, the solvent was removed in vacuo, and the residue was taken up in ethyl acetate, washed 3× each with 5% $KHSO_4$, saturated $NaHCO_3$ solution and NaCl-saturated water and then dried over $Na_2SO_4$. The solvent was removed in vacuo. A pale oil remained as residue and crystallized overnight in a refrigerator.

Yield: 3.2 g (8.17 mmol), HPLC: 51.69% B

1b) H-Pzd-βAla-Z×HCl 3.2 g (8.17 mmol) of Boc-Pzd-βAla-Z were partly dissolved in glacial acetic acid, mixed with 50 ml of 1N HCl in glacial acetic acid and left to stand at room temperature, shaking occasionally, for 1 h. The solvent was partly removed in vacuo, and the product was precipitated by adding diethyl ether, and was filtered off with suction, washed again with diethyl ether and dried in vacuo.

Yield: 2.13 g (6.5 mmol) of white solid, HPLC: 28.19% B

1c) Boc-Phe(3-CN)—OH 2.5 g (13.1 mmol) of H-Phe(3-CN)—OH were dissolved in 100 ml of dioxane and, at 0° C., 13 ml (13 mmol) of 1N NaOH and 3.16 g (14.5 mmol) of Boc pyrocarbonate were added. The mixture was stirred at 0° C. for 20 min and then at room temperature for 4 h, during which a total of 7 ml (7 mmol) of 1N NaOH was added in portions, thus keeping the pH constant at 8-8.5. The solvent was removed in vacuo, and the residue was taken up in ethyl acetate, washed in each case 3× with 5% $KHSO_4$ and 3× with NaCl-saturated water and then dried over $Na_2SO_4$. The solvent was removed in vacuo. A white solid was obtained as residue.

Yield: 2.11 g (7.3 mmol) of white solid, HPLC: 45.93% B

1d) Boc-Phe(3-AcOxam)-OH 2.11 g (7.3 mmol) of Boc-Phe(3-CN)—OH were dissolved in 100 ml of methanol, and 760 mg (10.95 mmol) of hydroxylamine×HCl and 1.9 ml (10.95 mmol) of DIEA were added. The mixture was stirred under reflux for 6 h. A further 266 mg (3.84 mmol) of hydroxylamine×HCl and 665 µl (3.84 mmol) of DIEA were added and the mixture was stirred under reflux for a further 3 h and then at room temperature overnight. The solvent was then removed in vacuo. A pale oil remained as residue and was dissolved in 50 ml of glacial acetic acid, and 2 ml (22 mmol) of acetic anhydride were added. The mixture was stirred at room temperature for 30 min. The solvent was removed in vacuo, and the residue was taken up in ethyl acetate, washed 3× each with 5% $KHSO_4$ and NaCl-saturated water and then dried over $Na_2SO_4$. The solvent was removed in vacuo.

Yield: 3.31 g (colorless oil), HPLC: 26.59% B

1e) Boc-Phe(3-AcOxam)-Pzd-βAla-Z 0.92 g (2.8 mmol) of H-Pzd-βAla-Z×HCl and 1.02 g (2.8 mmol) of Boc-Phe(3-AcOxam)-OH were dissolved in 40 ml of DMF and, at 0° C., 1.46 g (2.8 mmol) of PyBop and 1.46 ml (8.4 mmol) of DIEA were added. The mixture was stirred at 0° C. for 20 min and at room temperature for a further. 2 h. The solvent was then removed in vacuo, and the residue was taken up in ethyl acetate, washed 3× each with 5% KHSO₄, saturated NaHCO₃ solution and NaCl-saturated water and then dried over Na₂SO₄. The solvent was removed in vacuo.

Yield: 2.49 g (pale oil), HPLC: 48.13% B

1f) H-Phe(3-AcOxam)-Pzd-βAla-Z×HCl 2.49 g of Boc-Phe(3-AcOxam)-Pzd-βAla-Z (crude product) were partially dissolved in glacial acetic acid, mixed with 30 ml of 1N HCl in glacial acetic acid and left to stand at room temperature, with occasional shaking, for 1 h. The solvent was partly removed in vacuo, and the product was precipitated by adding diethyl ether, and was filtered off with suction, washed again with diethyl ether and dried in vacuo.

Yield: 1.32 g (2.3 mmol) of white solid, HPLC: 32.89% B

1g) Anthracenesulfonyl-Phe(3-AcOxam)-Pzd-βAla-Z

At 0° C. 207.7 mg (0.361 mmol) of H-Phe(3-AcOxam)-Pzd-βAla-Z, 127 μl (0.73 mmol) of DIEA and 100 mg (0.361 mmol) of anthracenesulfonyl chloride (Fluka) Were dissolved in 10 ml of DMF. The mixture was stirred at 0° C. for 20 min and then at room temperature overnight. The solvent was removed in vacuo, and the residue was taken up in ethyl acetate, washed 3× each with 5% KHSO₄, saturated NaHCO₃ solution and NaCl-saturated water and then dried over Na₂SO₄. The solvent was removed in vacuo. A pale oil remained as residue and was employed directly, without further purification, for the next synthesis step

HPLC: 57.65% B

1h) Anthracenesulfonyl-Phe(3-Am)-Pzd-βAla

The crude product 1g was dissolved in 50 ml of 90% acetic acid and 5 ml of 1 N HCl, and 30 mg of catalyst (10% Pd/C) were added. The mixture was hydrogenated with hydrogen under atmospheric pressure at 40° C. overnight. The catalyst was then filtered off, and the solvent was concentrated in vacuo. Part of the crude product was purified by preparative reversed phase HPLC.

HPLC: 34.11% B

MS: calculated 586.24 (monoisotopic). found 587.79 [M+H]⁺

Example 2

Synthesis of anthracenesulfonyl-Phe(3-Am)-Pzd-CO—CH₂—CH₂-guanidino×2 TFA (Compound 11 from Table 1)

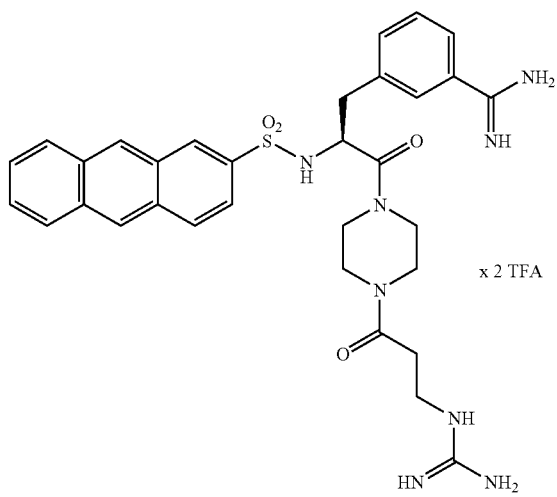

2a) Anthracenesulfonyl-Phe(3-Am)-Pzd-CO—CH₂—CH₂-guanidino

About 115 mg of anthracenesulfonyl-Phe(3-Am)-Pzd-βAla crude product (1h) were dissolved in 10 ml of DMF and 90.3 mg (0.616 mmol) of pyrazolecarboxamidine×HCl and 107 μl (0.616 mmol) of DIEA were added. The mixture was stirred overnight and then the solvent was removed in vacuo. The remaining residue was dried in vacuo and purified by preparative reversed phase HPLC without further purification.

HPLC: 35.09% B

MS: calculated 628.26 (monoisotopic). found 629.4 [M+H]⁺

Example 3

Synthesis of 2,4,6-triisopropylphenylsulfonyl-Phe(3-Am)-iNip-DAE-H×2 TFA (Compound 3 from Table 1)

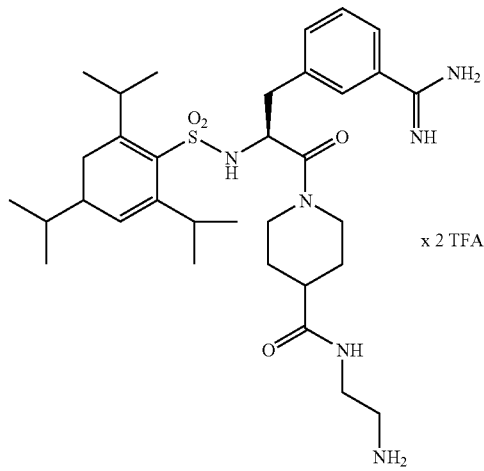

3a) Tips-Phe(3-CN)—OH

A solution of 1 eq. of Tips-Cl (97% pure, 4.69 g, 15 mmol) in dioxane was added dropwise to a solution of 1.05 eq. of H-L-Phe(3-CN)—OH (3 g, 15.8 mmol) in dioxane and 2.1 eq. of 1M NaOH (31.5 ml) while stirring at RT. The pH of the solution was monitored during this and kept at pH 8-9 with 1M NaOH. After 4 h, the solvent was removed in vacuo, and the residue was taken up in ethyl acetate and subjected to 3 acidic (5% KHSO₄) and 3 neutral (saturated NaCl solution) washes. The organic phase was dried over Na₂SO₄, the solvent was removed in vacuo, and the resulting product was recrystallized from ethyl acetate/hexane (yellowish crystalline compound).

Yield: 6.6 g (96.3%)

HPLC: 71.1% B

3b) Tips-Phe(3-OAm)—OH 1 eq. of Tips-Phe(3-CN)—OH (3 g, 6.6 mmol), 1.5 eq. of hydroxylamine×HCl (685 mg, 9.9 mmol) and 3 eq. of DIEA (3.4 ml, 19.8 mmol) were dissolved in absolute ethanol and boiled under reflux for 4 h, and then stirred at RT while metering in further hydroxylamine×HCl and base (DIEA, pH 8-9) until starting material was no longer found in the HPLC. After removal of the solvent, the residue was taken up in ethyl acetate and subjected to 3 acidic (5% KHSO$_4$) and 3 neutral (saturated NaCl solution) washes. The organic phase was dried over Na$_2$SO$_4$, the solvent was removed in vacuo, and the resulting product was recrystallized from ethyl acetate/hexane.

Yield: 1.63 g (white crystals; 50.4%),
HPLC: 51.0% B

3c) Tips-Phe(3-AcOAm)—OH 1 eq. of Tips-Phe(3-OAm)—OH (2.5 g, 5.1 mmol) was dissolved in 100 ml of glacial acetic acid and then 1.5 eq. of acetic anhydride (724 µl, 7.6 mmol) were added and the mixture was stirred for 15 min. After removal of the solvent in vacuo, the product is obtained as a white powder.

Yield: 2.7 g (99.4%)
HPLC: 64.5% B

3d) H-iNip-DAE-Z×HCl 497 mg (2.17 mmol) of Boc-isonipecotic acid were dissolved with 250 µl (2.27 mmol) of NMM in 10 ml of dry THF. 296 µl (2.27 mmol) of isobutyl chloroformate were added at −15° C., and the mixture was stirred for a further 10 min. Then 500 mg (2.17 mmol) of N-Z-1,2-diaminoethane×HCl and 250 µl (2.27 mmol) of NMM were added, and the mixture was stirred at −15° C. for a further 1 h and then at RT for 4 h. The solvent was removed in vacuo, and the residue was taken up in ethyl acetate and subjected to 3 acidic (5% KHSO$_4$), 1 neutral (saturated NaCl solution), 3 basic (NaHCO$_3$ saturated) and 3 neutral (saturated NaCl solution) washes. The ethyl acetate phase was then dried over Na$_2$SO$_4$, and the solvent was removed in vacuo, resulting in the product as amorphous substance (HPLC: 50.3% B). The crude product was dissolved in 20 ml 1 N of hydrogen chloride in glacial acetic acid and left to stand at RT for 1 h. The solvent was then removed in vacuo, and the product was lyophilized.

Yield: 722 mg
HPLC: 26.4% B

3e) Tips-Phe(3-Am)-iNip-DAE-H×2 TFA 150 mg (0.28 mmol) of Tips-Phe(3-AcOAm)—OH were dissolved with 97 mg (0.28 mmol) of H-iNip-DAE-Z×HCl in 5 ml of DMF and cooled to 0° C. in an ice bath while stirring. 122 µl (0.70 mmol) of DIEA and 154 mg (0.29 mmol) of PyBOP were added to the cooled solution. After 15 min, the ice bath was removed and the mixture was stirred at RT for a further 2 h. The solvent was then removed in vacuo, and the residue was taken up in ethyl acetate and subjected to 3 acidic (5% KHSO$_4$), 1 neutral (saturated NaCl solution), 3 basic (NaHCO$_3$ saturated) and 3 neutral (saturated NaCl solution) washes. The ethyl acetate phase was then dried over Na$_2$SO$_4$, and the solvent was removed in vacuo. The residue was dissolved in 90% strength glacial acetic acid, mixed with 10 percent by weight catalyst (10% Pd/C) and hydrogenated with hydrogen at RT overnight. The catalyst was filtered off, and the solvent was removed to dryness in vacuo, and the residue was purified by preparative reversed phase HPLC.

Yield: 92 mg
HPLC: 43.3% B
MS: calculated 626.36 (monoisotopic). found 628.1 [M+H]$^+$ Example 4

Synthesis of 2,4,6-triisopropylphenylsulfonyl-Phe (3Am)-iNip-NH—CH$_2$—CH$_2$-guanidino×2 TFA (Compound 34 from Table 1)

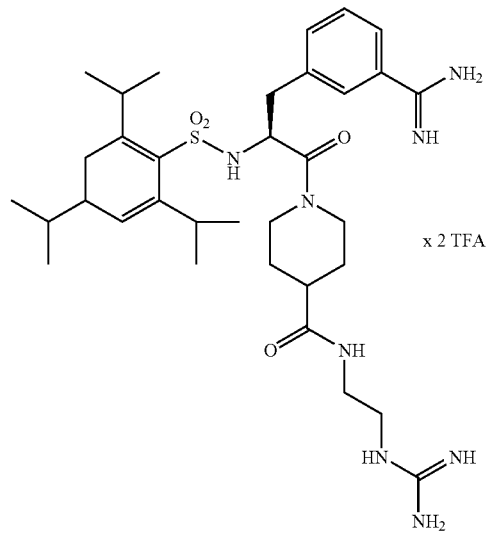

4a) Tips-L-Phe(3-Am)-iNip-NH—CH$_2$—CH$_2$-guanidino×2 TFA 85 mg (0.1 mmol) of Tips-Phe(3-Am)-iNip-DAE-H×2 TFA were dissolved in 5 ml of DMF and 30 mg (0.2 mmol) of pyrazolecarboxamidine and 55 µl (0.3 mmol) of DIEA were added. The mixture was stirred at RT overnight. The solvent was then removed in vacuo, and the residue was purified by preparative reversed phase HPLC.

HPLC: 43.7% B
MS: calculated 668.38 (monoisotopic). found 669.8 [M+H]$^+$

Example 5

Synthesis of 2-Nas-Phe(3-Am) 4(aminoethyl)piperidide×2 TFA (Compound 36 from Table 1)

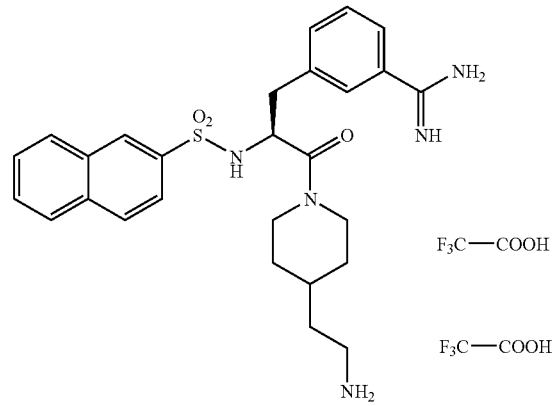

5a) 2-Nas-Phe(3-CN)—OH 2.49 g (11 mmol) of 2-Nas chloride (dissolved in dioxane) were added dropwise over a period of 30 min to 1.9 g (10 mmol) of H-Phe(3CN)—OH, dissolved in 100 ml of dioxane/water mixture and 22 ml of 1 N NaOH solution, at 0° C. The mixture was stirred at 0° C. for 1 h and further at room temperature overnight. The solvent was then removed in vacuo, and the residue was dissolved in water (adjusted to pH 8-9 with NaOH). The aqueous phase was extracted 2× with diethyl ether and then the pH was adjusted to pH 3-4 with 1 N HCl. The product was extracted 3× with ethyl acetate, and the ethyl acetate phase was washed 3× each with 5% KHSO₄ and NaCl-saturated water and then dried over Na₂SO₄. The solvent was removed in vacuo. A pale oil remained and crystallized in a refrigerator.

Yield: 3.51 g (9 mmol), HPLC: 51.02% B 5b) 2-Nas-Phe(3-AcOxam)-OH 3.5 g (9 mmol) of 2-Nas-Phe(3CN)—OH were dissolved in 100 ml of methanol, and 1.04 g (15 mmol) of hydroxylamine× HCl and 2.61 ml (15 mmol) of DIEA were added. The mixture was stirred under reflux for 6 h. Then a further 700 mg (10 mmol) of hydroxylamine×HCl and 1.74 ml (10 mmol) of DIEA were added. The mixture was stirred under reflux for a further 4 h and then at room temperature overnight. The solvent was then removed in vacuo. A pale oil remained as residue and was dissolved in 50 ml of glacial acetic acid and mixed with 2.83 ml (30 mmol) of acetic anhydride. The mixture was stirred at room temperature for 1 h. The solvent was removed in vacuo, and the residue was taken up in ethyl acetate, washed 1× with 5% KHSO₄ solution and 3× with NaCl-saturated water and then dried over Na₂SO₄. The solvent was virtually removed in vacuo. The product began slowly to crystallize and was filtered off with suction.

Yield: 3.02 g (6.64 mmol) of pale solid, HPLC: 44.04% B 5c) 2-Nas-Phe(3-AcOxam) 4(aminoethyl)piperidide×HCl 100 mg (0.22 mmol) of 2-Nas-Phe(3-AcOxam)-OH and 50 mg (0.22 mmol) of 4-(2-Boc-aminoethyl)piperidine (Tyger Scientific Inc., Princeton, N.Y.) were dissolved in 10 ml of DMF and, at 0° C., 115 mg (0.22 mmol) of PyBop and 115 µl (0.22 mmol) of DIEA were added. The mixture was stirred at 0° C. for 20 min and at room temperature for a further 3 h. The solvent was then removed in vacuo. The residue was taken up in ethyl acetate, washed 2× with 5% KHSO₄ solution, 1× with NaCl-saturated water, 2× with sat. NaHCO₃ solution and 3× with NaCl-saturated water and then dried over Na₂SO₄. The solvent was removed in vacuo.

The crude product was partly dissolved in glacial acetic acid, mixed with 5 ml of 1N HCl in glacial acetic acid and left to stand at room temperature, shaking occasionally, for 1 h. The solvent was removed in vacuo, a pale oil remaining.

Yield: 105 mg of oil, HPLC: 35.66% B 5d) 2-Nas-Phe(3-Am) 4(aminoethyl)piperidide×2 TFA The crude product 5c was dissolved in 50 ml of 90% acetic acid, and 15 mg of catalyst (10% Pd/C) were added. The mixture was hydrogenated with hydrogen under atmospheric pressure at 40° C. overnight. The catalyst was then filtered off, and the solvent was concentrated in vacuo. A third of the crude product was purified by preparative reversed phase HPLC.

Yield: 17.6 mg HPLC: 29.03% B

MS: calculated 507.23 (monoisotopic). found 508.4 [M+H]⁺

Example 6

Synthesis of 2-Nas-Phe(3-Am) 4(guanidinoethyl)piperidide×2 TFA (Compound 37 from Table 1)

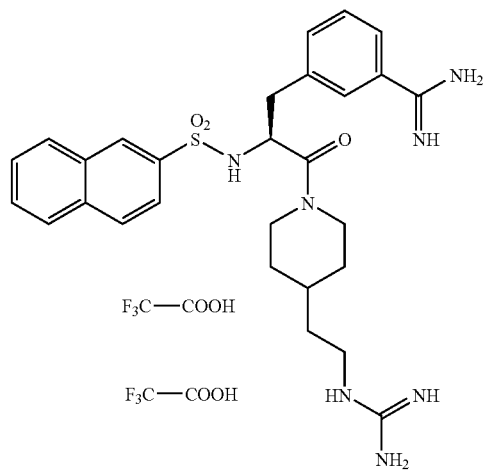

6a) 2-Nas-Phe(3-Am) 4(guanidinoethyl)piperidide×2 TFA

About 80 mg of 2-Nas-Phe(3-AcOxam) 4(aminoethyl)piperidide×HCl crude product (5d) were dissolved in 5 ml of DMF, and 65 mg (0.45 mmol) of pyrazolecarboxamidine× HCl and 105 µl (0.6 mmol) of DIEA were added. After 3 h, a further 21.5 mg (0.15 mmol) of pyrazolecarboxamidine×HCl and 35 µl (0.15 mmol) of DIEA were added, and the mixture was stirred further overnight. The solvent was removed in vacuo, and the remaining residue was purified by preparative reversed phase HPLC.

Yield: 42 mg HPLC: 31.19% B

MS: calculated 549.25 (monoisotopic). found 550.4 [M+H]⁺

Example 7

Preparation of the Catalytic Domain of Matriptase

Cloning: The catalytic domain of matriptase was amplified by PCR using the following primer pair:

Sense primer:

5'-GGCAATTCCATATGAAACATCACCATCATCACCATGTTGTTGGGGGC ACGGATGCG-3'

Antisense primer:

5'-GCATGAATTCTTATACCCCAGTTCTCTTTGATCCA-3

Sense primer and antisense primer were chosen so that an Nde1 cleavage site (bold) followed by the peptide sequence Met Lys (His)₆ was introduced at the 5' end in front of the protease domain (italic), and an EcoR1 cleavage site (bold)

was inserted at the 3' end of matriptase (italic). The PCR product was cloned via NdeI and EcoR1 into pET24 (Novagen), a vector for expression in *Escherichia coli*.

The catalytic domain of matriptase was expressed in inactive and insoluble form in *Escherichia coli*, and was purified, refolded and then activated. The steps were in detail:

Expression and purification: BL21 (DE3) cells (Novagen) which contained the vector from the cloning described above were incubated in LB, 30 μg/ml kanamycin at 37° C. and 250 rpm. Expression was induced at an $OD_{600}$ of 0.6 by adding 1 mM IPTG, and incubation was continued for one hour. The cells were then pelleted and disrupted with 5 ml Bug Buster™ protein extraction reagent (Novagen), and the DNA was digested with 25 U/ml per 1 g of cell pellet of Benzonase® nuclease (Novagen). The protein aggregates were washed and denatured with 5 ml of denaturation buffer (6 M guanidinium HCL, 10 mM Tris HCl, 100 mM Na phosphate, pH 8.0) per 1 g of pellet. Insoluble constituents were removed by centrifugation (16 000 g, 30 min, 20° C.), and the supernatant was filtered (0.2 μm), mixed with 10 mM β-mercaptoethanol and then put onto a metal chelate chromatography column (1 ml NiNTA (Qiagen) per 10 ml of supernatant) to purify the catalytic domain of matriptase. The column was washed (8 M urea, 10 mM Tris HCl, 100 mM Na phosphate, pH 6.3), and the partially purified protein was eluted with 8 M urea, 10 mM Tris HCl, 100 mM Na phosphate, pH 4.5.

Refolding: The matriptase-containing fractions were combined, derivatized with glutathione and then diluted for the refolding in a final concentration of 50 μg/ml in refolding buffer (50 mM Tris HCl, 0.5 M L-arginine, 20 mM $CaCl_2$, 1 mM EDTA, 0.1 M NaCl, pH 7.5). After incubation at room temperature for 3 days, the refolding mixture was filtered and concentrated to a concentration of >300 μg/ml (Centricon Plus-80, Amicon), and the buffer was changed to activation buffer (20 mM Na phosphate, 150 mM NaCl, pH 7.0) by gel filtration (PD 10 columns, Pharmacia).

Activation: Since a correctly processed N terminus is a precondition for the activity of serine proteases, it was necessary to delete the peptide $MK(His)_6$ to activate the refolded matriptase. For this purpose, the refolding mixture was incubated with 2.5 mU per 50 μg of protein of activated DAPase™ (Qiagen) at 30° C. for 2 h, and the activated matriptase was separated from the non-activated matriptase and the DAPase by metal chelate chromatography.

The yield of active matriptase was about 0.9 mg/l of bacterial culture. The proteolytic activity was detected by cleavage of the chromogenic substrate Pefachrome tPA (Pentapharm).

Example 8

Determination of the Inhibitory Effect of Matriptase with the Inhibitors Listed in Table 1

To determine the inhibitory effect, 200 μl of Tris buffer (0.05 M, 0.154 M NaCl, 5% ethanol, pH 8.0; contains the inhibitor), 25 μl of substrate ($CH_3SO_2$-D-HHT-Gly-Arg-pNA; 2 and 1 mM) and 50 μl of matriptase (0.5 μg/ml) were incubated at 25° C. After 3 min the reaction was stopped by adding 25 μl of acetic acid (50%), and the absorption at 405 nm was determined using a Microplate Reader (Dynatech MR 5000). The $K_i$ values were found by the Dixon method (Biochem. J. 55, 170-171, 1953) by egression using a computer program. The $K_i$ values (Table 1) are the average of three determinations.

TABLE 1

Determination of the $K_i$ values for the inhibition of matriptase

| No. | Structure of inhibitor | $K_i/\mu M$ |
|---|---|---|
| 1 | 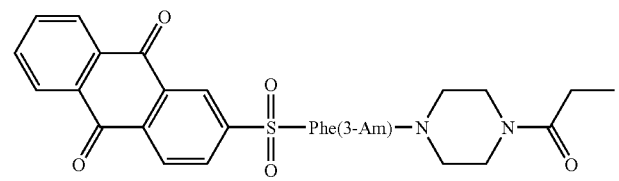 | 1.5 |
| 2 | 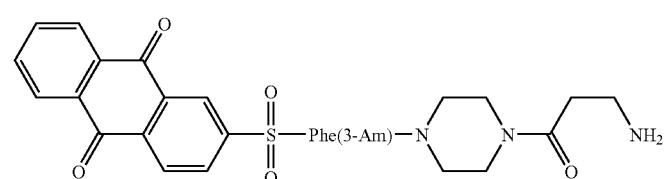 | 0.16 |
| 3 | 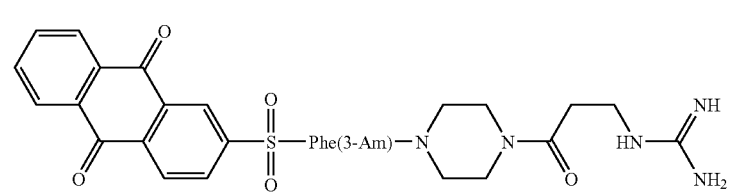 | 0.053 |

TABLE 1-continued

Determination of the K_i values for the inhibition of matriptase

| No. | Structure of inhibitor | $K_i/\mu M$ |
|---|---|---|
| 4 | 2,4,6-triisopropylphenyl-SO₂-Phe(3-Am)-N(piperazine)N-C(O)-CH₂CH₂-NH₂ | 0.14 |
| 5 | 2,4,6-triisopropylphenyl-SO₂-Phe(3-Am)-N(piperazine)N-C(O)-CH₂CH₂-NH-C(=NH)NH₂ | 0.057 |
| 6 | 2,4,6-triisopropylphenyl-SO₂-Phe(3-Am)-N(piperazine)N-C(O)-CH₂CH₂CH₂-NH₂ | 0.14 |
| 7 | 2,4,6-triisopropylphenyl-SO₂-Phe(3-Am)-N(piperazine)N-C(O)-CH₂CH₂CH₂-NH-C(=NH)NH₂ | 0.056 |
| 8 | 2,4,6-triisopropylphenyl-SO₂-Phe(3-Am)-N(piperazine)N-C(O)-CH₂-NH₂ | 0.69 |
| 9 | 2,4,6-triisopropylphenyl-SO₂-Phe(3-Am)-N(piperazine)N-C(O)-CH₂-NH-C(=NH)NH₂ | 0.33 |

TABLE 1-continued

Determination of the K_i values for the inhibition of matriptase

| No. | Structure of inhibitor | $K_i/\mu M$ |
|---|---|---|
| 10 | anthracene-SO2-Phe(3-Am)-N(piperazine)N-C(O)-CH2CH2-NH2 | 0.27 |
| 11 | anthracene-SO2-Phe(3-Am)-N(piperazine)N-C(O)-CH2CH2-NH-C(=NH)NH2 | 0.044 |
| 12 | naphthalene-SO2-Phe(3-Am)-N(piperazine)N-C(O)-CH2CH2-NH2 | 0.83 |
| 13 | naphthalene-SO2-Phe(3-Am)-N(piperazine)N-C(O)-CH2CH2-NH-C(=NH)NH2 | 0.21 |
| 14 | tetrahydronaphthalene-SO2-Phe(3-Am)-N(piperazine)N-C(O)-CH2CH2-NH2 | 0.40 |
| 15 | tetrahydronaphthalene-SO2-Phe(3-Am)-N(piperazine)N-C(O)-CH2CH2-NH-C(=NH)NH2 | 0.3 |
| 16 | tetrahydronaphthalen-1-yl-SO2-Phe(3-Am)-N(piperazine)N-C(O)-CH2CH2-NH2 | 0.99 |
| 17 | 4-cyclohexylphenyl-SO2-Phe(3-Am)-N(piperazine)N-C(O)-CH2CH2-NH2 | 0.14 |
| 18 | 4-cyclohexylphenyl-SO2-Phe(3-Am)-N(piperazine)N-C(O)-CH2CH2-NH-C(=NH)NH2 | 0.089 |
| 19 | biphenyl-SO2-Phe(3-Am)-N(piperazine)N-C(O)-CH2CH2-NH2 | 0.60 |

TABLE 1-continued

Determination of the $K_i$ values for the inhibition of matriptase

| No. | Structure of inhibitor | $K_i/\mu M$ |
|---|---|---|
| 20 | | 0.25 |
| 21 | | 0.47 |
| 22 | | 0.2 |
| 23 | | 3.3 |
| 24 | | 0.73 |
| 25 | | 2.4 |
| 26 | | 0.4 |
| 27 | | 0.46 |

TABLE 1-continued

Determination of the $K_i$ values for the inhibition of matriptase

| No. | Structure of inhibitor | $K_i/\mu M$ |
| --- | --- | --- |
| 28 | 2,4,6-triisopropylphenyl-SO$_2$—Phe(3-Am)—piperazine—C(O)—piperidine-4-yl(NH) | 0.11 |
| 29 | 2,4,6-triisopropylphenyl-SO$_2$—Phe(3-Am)—piperazine—C(O)—piperidine-4-yl(N-C(=NH)NH$_2$) | 0.014 |
| 30 | anthraquinone-2-SO$_2$—Phe(3-Am)—piperidine-4-C(O)NH—CH$_2$CH$_2$—NH$_2$ | 0.021 |
| 31 | anthraquinone-2-SO$_2$—Phe(3-Am)—piperidine-4-C(O)NH—CH$_2$CH$_2$—NH—C(=NH)NH$_2$ | 0.013 |
| 32 | 9,10-dihydroxyanthracene-2-SO$_2$—Phe(3-Am)—piperidine-4-C(O)NH—CH$_2$CH$_2$—NH—C(=NH)NH$_2$ | 0.0098 |
| 33 | 2,4,6-triisopropylphenyl-SO$_2$—Phe(3-Am)—piperidine-4-C(O)NH—CH$_2$CH$_2$—NH$_2$ | 0.38 |

TABLE 1-continued
Determination of the K_i values for the inhibition of matriptase
| No. | Structure of inhibitor | $K_i/\mu M$ |
|---|---|---|
| 34 | 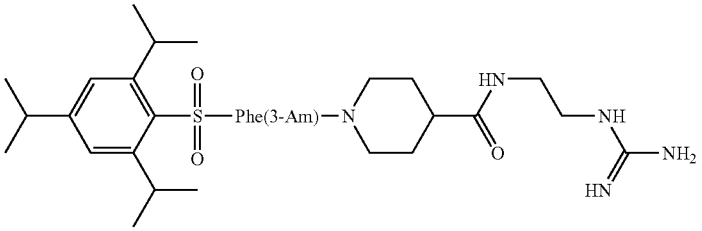 | 0.14 |
| 35 | 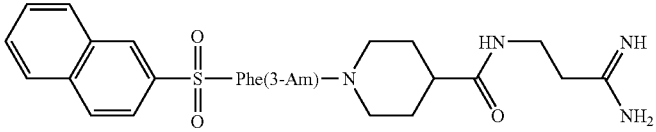 | 0.16 |
| 36 | 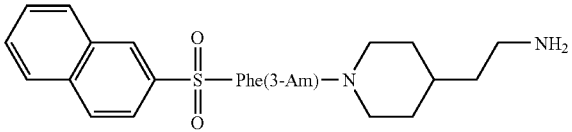 | 0.11 |
| 37 | 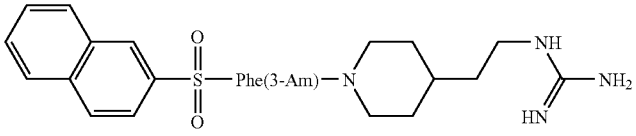 | 0.046 |
| 38 | 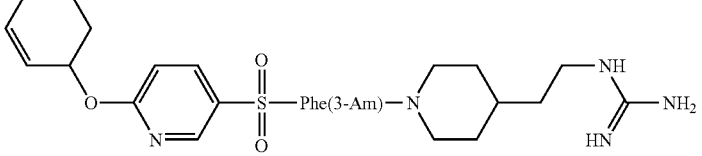 | 0.013 |
| 39 | 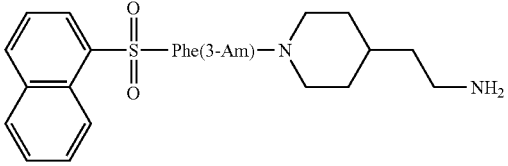 | 0.17 |
| 40 | 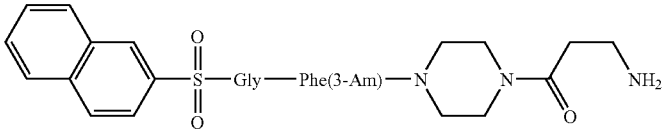 | 7.2* |
| 41 | 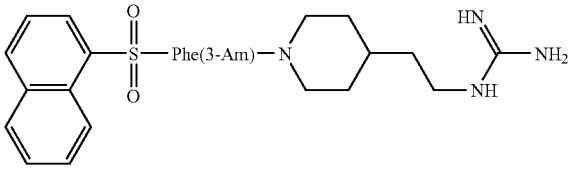 | 0.074 |
| 42 | 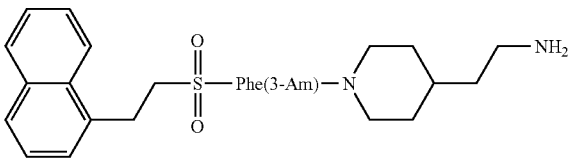 | 0.36 |

TABLE 1-continued

Determination of the $K_i$ values for the inhibition of matriptase

| No. | Structure of inhibitor | $K_i/\mu M$ |
|---|---|---|
| 43 | Naphthyl-CH₂CH₂-SO₂-Phe(3-Am)-N(piperidine-4-CH₂CH₂)-NH-C(=NH)-NH₂ | 0.18* |
| 44 | Naphthyl-SO₂-Gly-Phe(3-Am)-N(piperidine-4-CH₂CH₂)-NH₂ | 21 |
| 45 | Cyclohexyl-C₆H₄-SO₂-Phe(3-Am)-N(piperidine-4-CH₂CH₂)-NH₂ | 0.14 |
| 46 | Cyclohexyl-C₆H₄-SO₂-Phe(3-Am)-N(piperidine-4-CH₂CH₂)-NH-C(=NH)-NH₂ | 0.088 |
| 47 | Naphthyl-SO₂-Gly-Phe(3-Am)-N(piperidine-4-C(=O))-NH-CH₂CH₂CH₂-NH-Z | 3.9 |
| 48 | Naphthyl-SO₂-Gly-Phe(3-Am)-N(piperidine-4-C(=O))-NH-CH₂CH₂CH₂-NH₂ | 0.36 |
| 49 | Naphthyl-SO₂-Gly-Phe(3-Am)-N(piperidine-4-C(=O))-NH-CH₂-C(=NH)-NH₂ | 0.16 |
| 50 | Morpholino-SO₂-C₆H₄-SO₂-Gly-Phe(3-Am)-N(piperazine)-C(=O)-CH₂-NH₂ | 3.5 |
| 51 | Morpholino-SO₂-C₆H₄-SO₂-Gly-Phe(3-Am)-N(piperazine)-C(=O)-CH₂CH₂-NH-C(=NH)-NH₂ | 0.89 |

TABLE 1-continued
Determination of the $K_i$ values for the inhibition of matriptase
| No. | Structure of inhibitor | $K_i/\mu M$ |
|---|---|---|
| 52 | 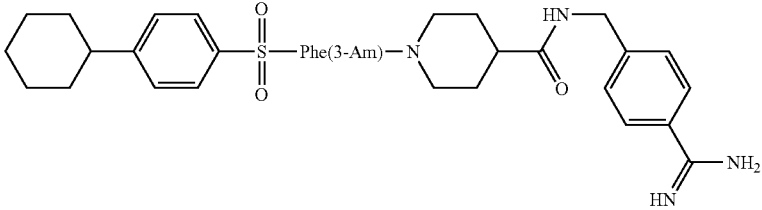 | |
| 53 | 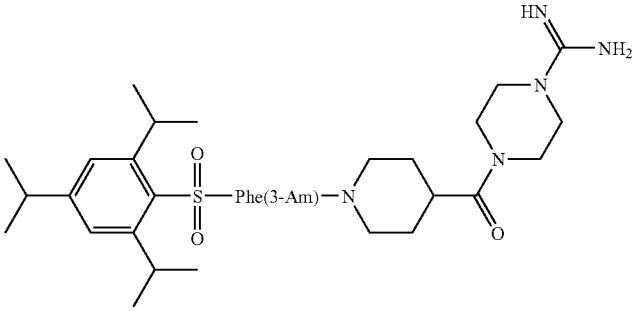 | 0.073 |
| 54 | 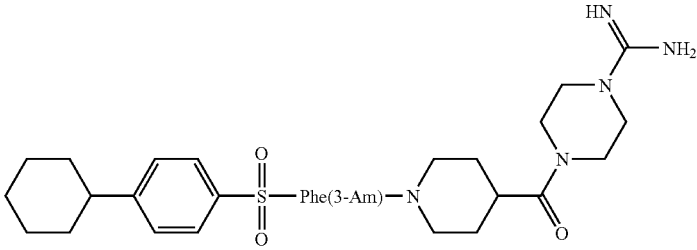 | 0.032 |
| 55 | 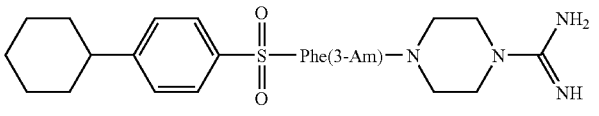 | 0.98 |
| 56 | 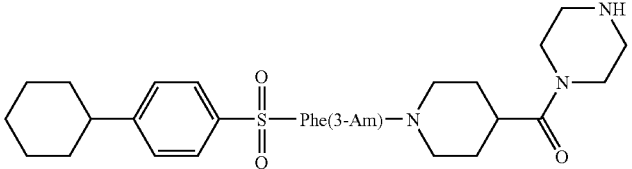 | 0.24 |
| 57 | 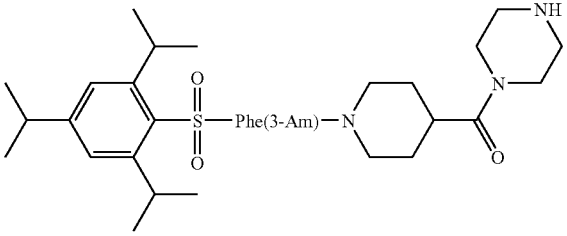 | 0.086 |
| 58 | 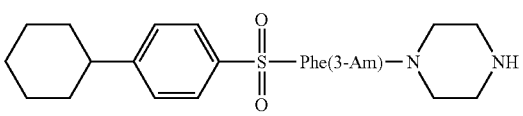 | 0.55 |

TABLE 1-continued
Determination of the $K_i$ values for the inhibition of matriptase
| No. | Structure of inhibitor | $K_i/\mu M$ |
|---|---|---|
| 59 | 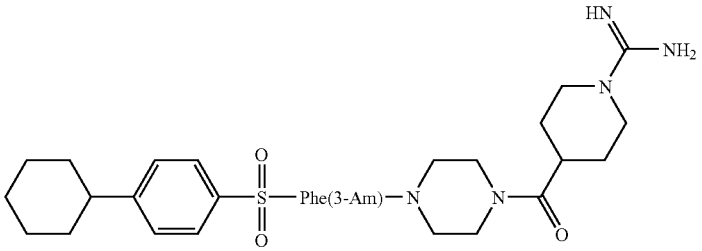 | 0.061 |
| 60 | 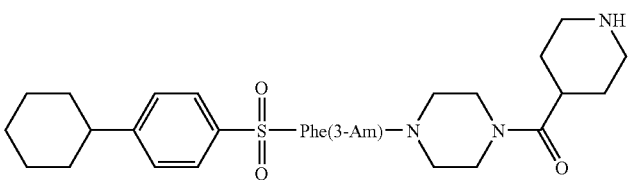 | 0.31 |
| 61 | 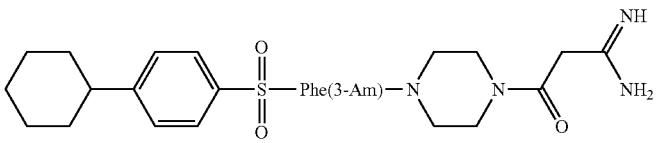 | 0.38 |
| 62 | 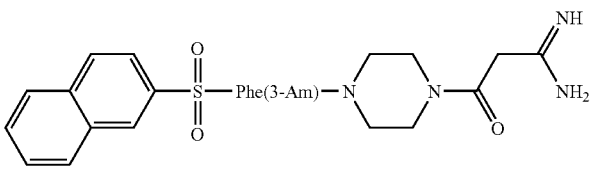 | 1.1 |
| 63 | 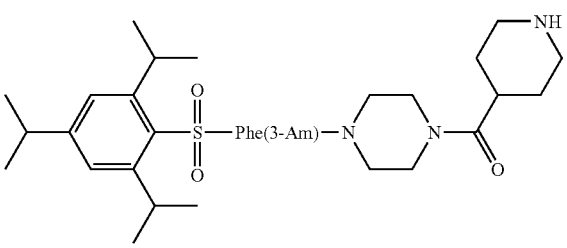 | 0.1 |
| 64 | 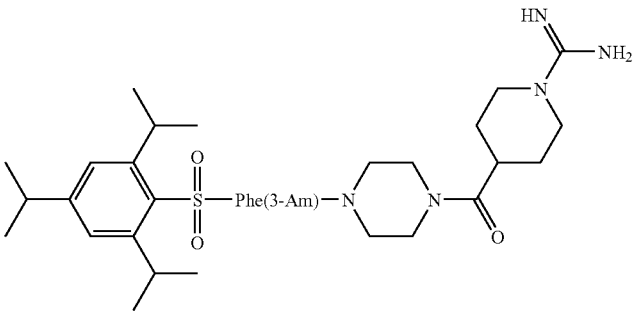 | 0.014 |

TABLE 1-continued
Determination of the K_i values for the inhibition of matriptase
| No. | Structure of inhibitor | $K_i/\mu M$ |
|---|---|---|
| 65 | 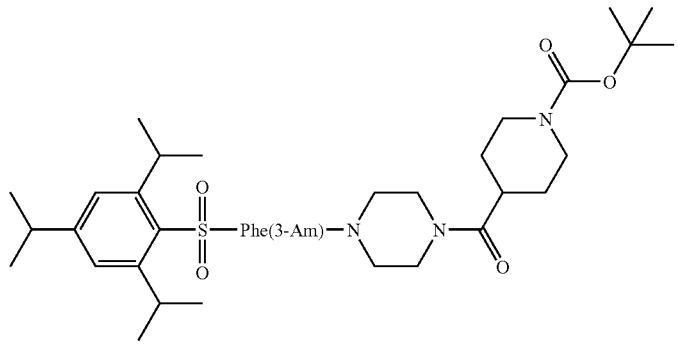 | 0.83 |
| 66 | 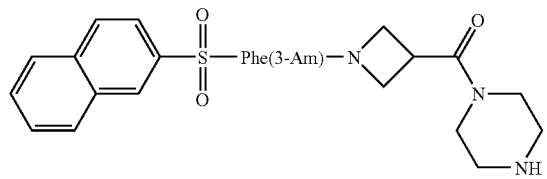 | 13 |
| 67 | 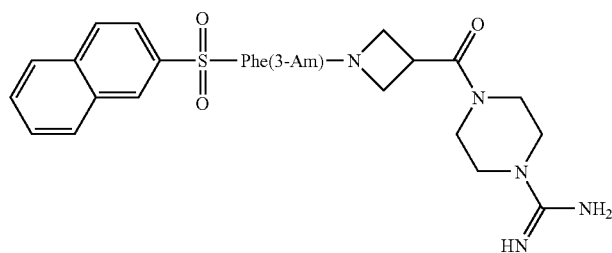 | 3.4 |
| 68 | 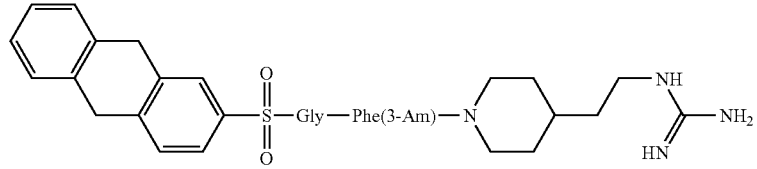 | 0.038 |
| 69 | 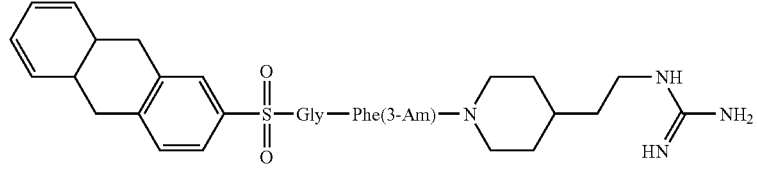 | 0.037 |
| 70 | 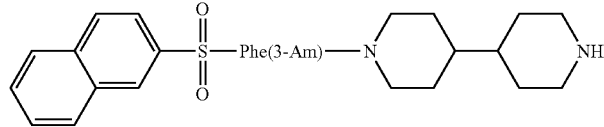 | 0.12 |
| 71 | 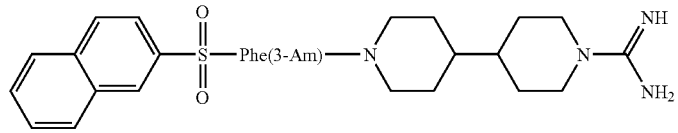 | 0.45 |

Example 9

Inhibition of Invasive Growth by Matriptase Inhibitors (Matrigel Assay)

A common test system for invasive growth at the cellular level is the Matrigel invasion assay. This entails cells being applied to an artificial extracellular matrix and investigation of how many cells migrate through the latter within a defined period.

It is shown here by way of example for the matriptase inhibitors 37 and 54 that invasive growth is influenced and the migration of matriptase-expressing colon carcinoma cell line DLD-1 through Matrigel is inhibited:

The wells of a 'Transwell' plate were each coated with 10 μg of Matrigel and 160 000 DLD-1 cells (Dexter et al, Cancer Research 39: 1020-1025 (1979)) in 100 μl of medium (RPMI 1640, with 2% Ultroser HY serum substituted) were applied to each, invasive growth was stimulated by adding ProHGF in 400 μl of medium with and without inhibitor (30 μM). After incubation at 37° C. and 5% $CO_2$ for 48 hours, the cells which had migrated through the matrix were fixed, stained and photographed at 100× magnification.

As FIG. 1 shows, the invasion of the DLD-1 cells through the extracellular matrix is stimulated by addition of proHGF. This indicates that the zymogen on the cell surface is activated. This effect is clearly inhibited by the matriptase inhibitors.

Example 10

Inhibition of Cell Scattering by Matriptase Inhibitors

Because of its ability to induce the detachment of cells from an isolated assemblage and the dissemination of the cells, HGF is also referred to as scatter factor. This function can be detected at the cellular level with the aid of the so-called scatter assay. This entails the cells being seeded and their dissemination stimulated by the addition of HGF being recorded after a defined time. HGF can be formed through activation of the inactive proform of HGF (proHGF). It is shown below by way of example for the matriptase inhibitors 37 and 54 that activation of proHGF by cellular matriptase is prevented and the scattering of proHGF-stimulated cells is reduced.

For this purpose, 500 matriptase-expressing prostate carcinoma cells (PC-3) were seeded in each well of a 96-well plate and incubated (37° C., 5% $CO_2$) in 100 μl of medium without fetal calf serum (Nut Mix. F-12, 2% Ultroser HY) overnight, and then the scattering was stimulated by adding proHGF with and without matriptase inhibitors (3 μM). After 6 days, the cells were fixed and stained, and representative sections were photographed at 100× magnification.

Figure 2:
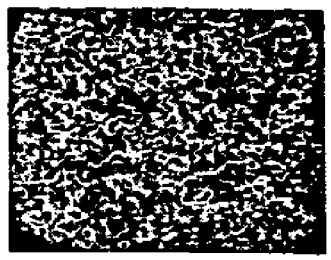
FIG. 2 shows the inhibition of the proHGF induced scatterings of PC-3 cells by the matriptase inhibitors 37 and 54 from Example 10.
Figure 2:
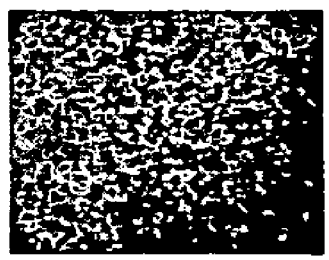
Figure 2:
Figure 2:
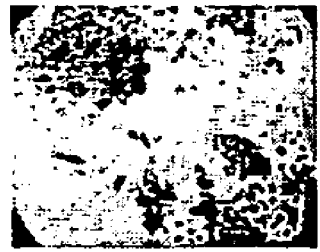
Figure 2:
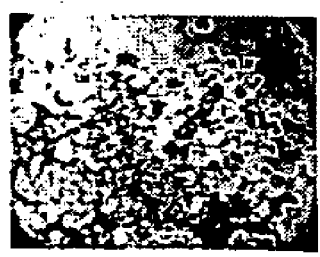
Figure 2:
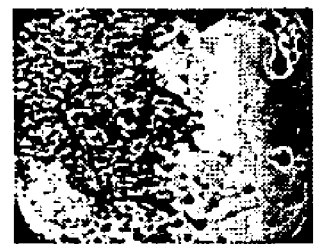

As FIG. 2 shows, the matriptase inhibitors 37 and 54 inhibit the proHGF-induced scattering of PC-3 cells.

In the concentrations used, neither proHGF nor the inhibitors have an influence on the proliferation of PC-3 cells. This indicates that the effect shown derives from an altered scattering behavior and not from an altered cell-doubling time.

The invention claimed is:

1. A compound of the formula (I''),

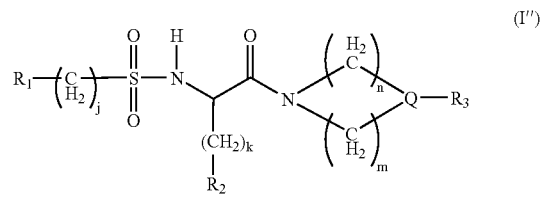

or a salt of this compound, wherein
optionally at least one of the methylene groups which are indexed with m or n in (I'') is substituted at least once by a hydroxyl, a halogen, a pseudohalogen, or a $COOR_2'$ group, and $R_2'$ is a linear, branched or cyclic alkyl group having 1 to 10 C atoms, and/or
optionally at least one of the C atoms of the methylene groups which are indexed with m or n in (I'') is replaced by S, N, or O, and/or
with retention of the imino group C-terminally linked to the sulfonylated amino acid, optionally at least one of the bonds forming the ring

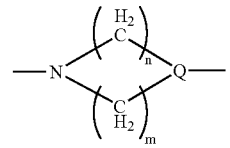

in (I'') is a double bond, and wherein
(i) $R_1$ is an optionally partially hydrogenated aryl or heteroaryl group comprising at least one of the atoms O, N, or S having 5 to 20 C atoms, or a linear, branched, or cyclic alkyl group having 1 to 10 C atoms, where $R_1$ is optionally substituted by
at least one halogen and/or pseudohalogen group, and/or
at least one linear, branched, or cyclic alkyl or alkyloxy or alkylthio group having 1 to 10 C atoms, which is optionally substituted at least once by a halogen, pseudohalogen, hydroxyl, amino, cyano, amidino, guanidine, or carboxyl group, where the carboxyl group is optionally esterified with a linear, branched, or cyclic alkyl group having 1 to 10 C atoms, and where the linear, branched, or cyclic alkyl group having 1 to 10 C atoms optionally comprises at least one heteroatom selected from the group consisting of O, N, and S, and/or
at least one aryl or heteroaryl group having 5 to 20 C atoms, where this aryl or heteroaryl group is optionally substituted by
at least one linear, branched or cyclic alkyl group having 1 to 10 C atoms and/or
at least one $COR_2'$ and/or $COOR_2'$ group, where $R_2'$ is a linear, branched, or cyclic alkyl group having 1 to 10 C atoms, and/or
at least one halogen group, and/or
at least one pseudohalogen group, and/or
at least one alkoxy group or one alkylthio group, where the alkyl radical has in each case 1 to 10 C atoms, and/or
at least one nitro group, and/or
at least one haloalkyl group having 1 to 10 C atoms, and where the aryl or heteroaryl group is linked via an alkylene group having 1 to 3 C atoms or via an oxygen atom or a sulfur atom to the radical $R_1$;

at least one hydroxyl, amino, cyano, amidino, guanidino, carboxyl, or carboxyalkyl group, where the amino group is optionally acylated and/or where the alkyl group of the carboxyalkyl group has 1 to 10 C atoms and/or the carboxyl group is optionally esterified with a linear, branched, or cyclic alkyl group having 1 to 10 C atoms or is amidated, and wherein said amidino is optionally substituted by a hydroxyl or a $C_1$-$C_6$-alkyloxycarbonyl group;

(ii) $R_2$ is an at least monosubstituted aryl group having 1 to 10 C atoms, where optionally at least one of these C atoms is replaced by S, N or O, at least one substituent is a group according to $R_4$, $R_2$ is optionally additionally substituted by a hydroxyl, $COR_2'$ or $COOR_2'$ group, and $R_2'$ is a linear, branched or cyclic alkyl group having 1 to 10 C atoms;

(iii) $R_3$ is a radical of the following formula (II):

where $A_1$ is either absent or an alkylene group having 1 to 4 C atoms which is optionally substituted by at least one halogen and/or pseudohalogen group, and/or at least one linear, branched, or cyclic alkyl group having 1 to 10 C atoms, and/or at least one aryl or one aralkyl group having 5 to 10 C atoms, and/or at least one cycloalkyl group having 3 to 10 C atoms, and/or at least one hydroxyl, cyano, alkyloxy or alkylthio having 1 to 10 C atoms, carboxyl or carboxyalkyl group, where the alkyl group of the carboxyalkyl group has 1 to 10 C atoms, and/or the carboxyl group is optionally esterified with a linear, branched or cyclic alkyl radical having 1 to 10 C atoms, or is amidated;

T is either absent or one of the following groups:

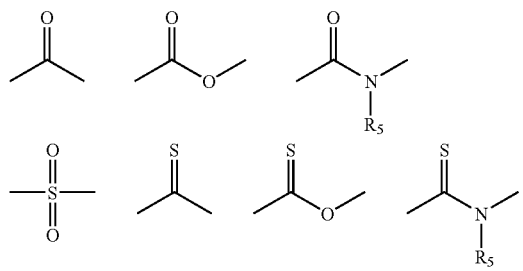

where $R_5$ is hydrogen or an alkyl group having 1 to 10 C atoms or an alkylene group having 1 to 6 C atoms, which forms with $A_2$ a ring optionally comprising at least one heteroatom;

$A_2$ is a linear, branched, or cyclic alkylene group having 1 to 10 C atoms or an aryl-, heteroaryl-, or aralkylene group having 1 to 10 C atoms, optionally comprising at least one heteroatom selected from the group consisting of N, S, and O, which is optionally substituted by at least one halogen and/or pseudohalogen group, and/or at least one linear, branched or cyclic alkyl group having 1 to 10 C atoms, and/or at least one aryl or one aralkyl group having 5 to 10 C atoms, and/or at least one cycloalkyl group having 3 to 10 C atoms, and/or at least one hydroxyl, cyano, alkyloxy or alkylthio group having 1 to 10 C atoms, carboxyl or carboxyalkyl group, where the alkyl group of the carboxyalkyl group has 1 to 10 C atoms, and/or the carboxyl group is optionally esterified with a linear, branched, or cyclic alkyl radical having 1 to 10 C atoms, or is amidated;

(iv) $R_4$ is one of the following, optionally modified basic groups:

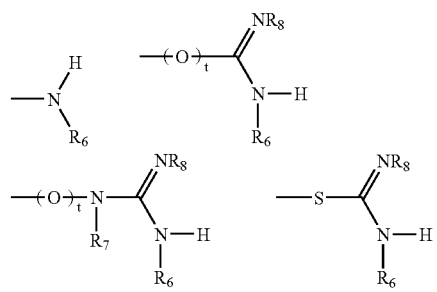

where t=0, 1; $R_6$ and $R_7$ are independently of one another hydrogen or an alkyl group having 1 to 6 C atoms or an alkylene group having 1 to 5 C atoms which forms a ring with $A_2$, or are a hydroxyl, amino, alkylamino, acyl, or alkyloxycarbonyl group, where the alkylamino, acyl, and alkyloxycarbonyl groups have independently of one another 1 to 6 C atoms, and where $R_8$ is hydrogen, an alkyl group having 1 to 3 C atoms, a hydroxyl group, or a $C_1$-$C_6$-alkyloxycarbonyl group, or is an alkylene group having 1 to 3 C atoms which forms a ring with $R_6$;

(v) Q is a CH group;

(vi) j=0, 1, or 2;

k=0, 1, 2, or 3; and m=n=2.

2. The compound as claimed in claim 1, characterized in that T is present and T is one of the groups defined as in claim 1, it being possible for the amide and ester groups to be incorporated in both orientations.

3. The compound as claimed in claim 1, where j=0 and $R_1$ is an at most disubstituted aryl radical.

4. The compound as claimed in claim 3, where the aryl radical is substituted via an oxygen bridge atom or a sulfur bridge atom or via a $C_1$-$C_3$ alkylene chain by a further aryl radical or a heteroaryl radical.

5. The compound as claimed in claim 4, where the aryl radical which is substituted via an oxygen bridge atom by a further aryl radical or a heteroaryl radical is a phenyl radical or a pyridyl radical.

6. The compound as claimed in claim 1, where the aryl radical or the heteroaryl radical has at least one substituent selected from the group of chlorine, fluorine, trifluoromethyl, methyl, and methoxy.

7. The compound as claimed in claim 3, where the aryl radical is substituted by at least one alkoxy group.

8. The compound as claimed in claim 1, where $R_1$ is selected from the group consisting of tert-butylphenyl, cyclohexylphenyl, 5,6,7,8-tetrahydronaphthyl, naphthyl, anthracyl, anthraquinoyl, anthrahydroquinoyl, pyridyloxyphenyl, phenyloxypyridyl, and pyridylalkylphenyl having a $C_1$-$C_3$-alkyl.

9. The compound as claimed in claim 1, where $R_2$ is an at least monosubstituted phenyl radical, thienyl radical, or pyridyl radical.

10. The compound as claimed in claim 1, where k=1 and $R_2$ is a phenyl radical meta-substituted by an amidino group, where the 3-amidinophenylalanine produced thereby has the L configuration.

11. The compound as claimed in claim 1, where $A_1$ is absent and T is

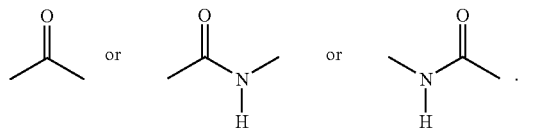

12. The compound as claimed in claim 2, where $A_2$ is a methylene, ethylene, or propylene group, and $R_4$ is selected from

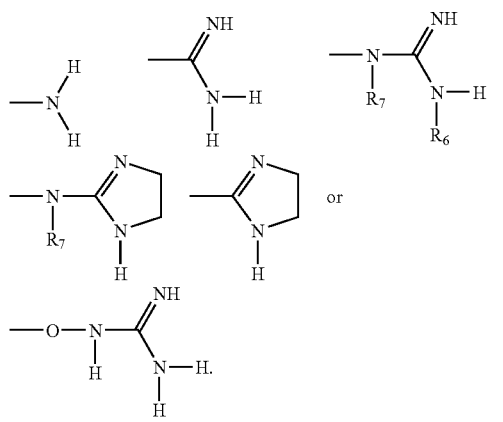

13. The compound as claimed in claim 2, where $R_3$ is a guanidinooxyalkyl radical or an aryl or heteroaryl radical, and where the aryl or heteroaryl radical is unsubstituted or substituted by at least one halogen, at least one methoxy radical, and/or at least one trifluoromethyl radical.

14. A process for preparing a compound as claimed in claim 1 or a compound (A1) or (A2), comprising the step (S1):

(S1) reaction of a compound of the general structure (E1')

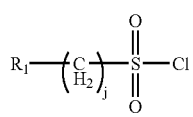

(E1')

with a compound of the general structure (E1')

(E1'')

to obtain a compound of the general structure (ZP1)

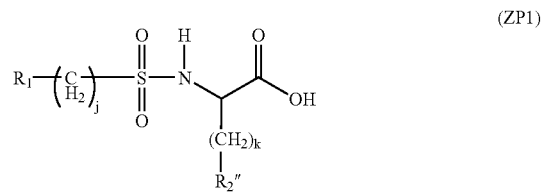

(ZP1)

where $R_2'$ is the aryl radical $R_2$ substituted either by $R_4$ or by $R_4$ protected with a suitable protective group, or by a substituent which is a precursor of $R_4$.

15. The process as claimed in claim 14, additionally comprising the step (S2''):

(S2'') reaction of the compound (ZP1) with a compound of the general structure (E3)

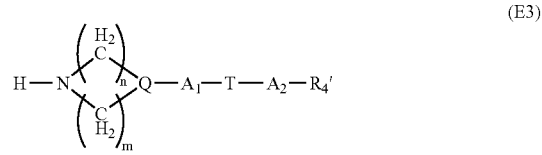

(E3)

where $R_4'$ is either $R_4$ or $R_4$ protected by a suitable protective group, or a precursor of $R_4$, to result in a compound of the general structure (P2)

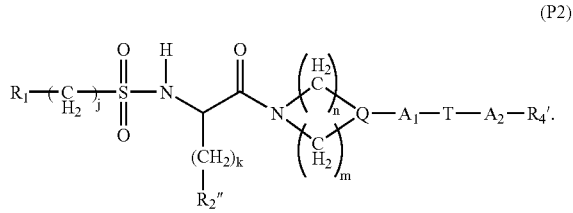

(P2)

16. The process as claimed in claim 14, where T=—(C=O)—NH—, Q=CH, and $A_1$ is absent, additionally comprising the steps (S2'''), (S3''') and (S4'''):

(S2''') reaction of a compound of the general structure (E3')

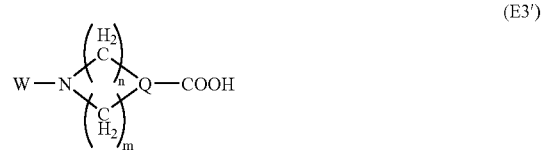

(E3')

with a compound of the general structure (E3''')

   (E3''')

to result in a compound of the general structure (ZP3)

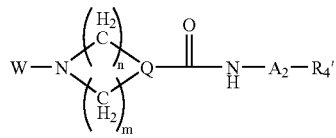   (ZP3)

(S3''') removal of the protective group W;
(S4''') reaction of the compound obtained in (S3''') with a compound (ZP1) to result in a compound of the general structure (P3)

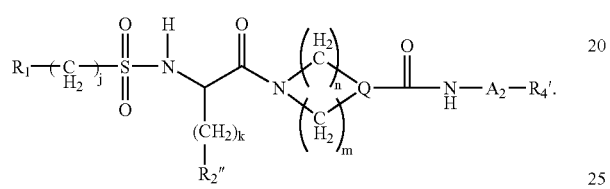   (P3)

17. The process as claimed in claim 14, additionally comprising the step of reacting the compound (ZP1) with a compound of the general structure (E2')

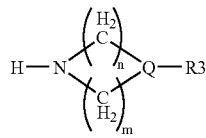   (E2')

where Q=N, m=n=2, and R3 is defined as in claim 12.

18. A pharmaceutical composition comprising at least one compound as claimed in claim 1, or a salt of this compound, and a pharmaceutically suitable excipient or additive.

19. The pharmaceutical composition of claim 18, characterized in that it is employed in the form of a tablet, a coated tablet, a capsule, a pellet, a suppository, a solution, in particular a solution for injection or infusion, eye drops, nose drops, or ear drops, a syrup, an emulsion or suspension, a pessary, a stick, an aerosol, a dusting powder, a paste, a cream, or an ointment.

20. The compound of claim 13, wherein the aryl radical is a benzyl or a phenoxy radical.

21. The compound of claim 13, wherein the heteroaryl radical is selected from a pyridinylmethylene, pyridinyloxo, pyrimidinyloxo, pyrazinyloxo, or pyridinylthio radical.

22. The compound of claim 1, wherein

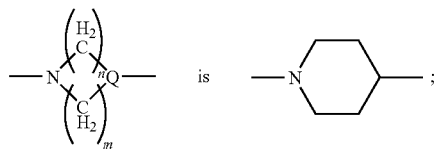

(i) $R_1$ is an optionally partially hydrogenated aryl group or a heteroaryl group comprising at least one of the atoms O, N, or S having 5 to 20 C atoms, where $R_1$ is optionally substituted by at least one linear, branched, or cyclic alkyl or alkyloxy or alkylthio group having 1 to 10 C atoms, and/or
at least one aryl or heteroaryl group having 5 to 20 C atoms, and where the aryl or heteroaryl group is linked via an alkylene group having 1 to 3 C atoms or via an oxygen atom or a sulfur atom to the radical $R_1$; and/or
at least one hydroxyl group;

(ii) $R_2$ is an at least monosubstituted aryl group having 1 to 10 C atoms, where at least one substituent is a group according to $R_4$;

(iii) $R_3$ is a radical of the following formula (II):

   (II)

where
$A_1$ is either absent or an alkylene group having 1 to 4 C atoms;
T is either absent or

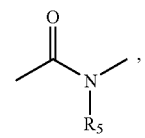

where $R_5$ is hydrogen or an alkyl group having 1 to 10 C atoms or an alkylene group having 1 to 6 C atoms, which forms with $A_2$ a ring optionally comprising at least one heteroatom;
$A_2$ is a linear, branched, or cyclic alkylene group having 1 to 10 C atoms; and (iv) $R_4$ is one of the following, optionally modified basic groups:

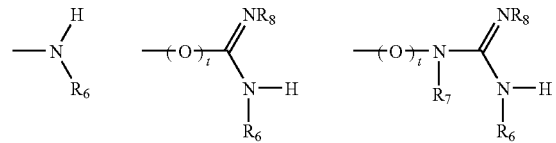

where t=0, 1; $R_6$ and $R_7$ are independently of one another hydrogen or an alkyl group having 1 to 6 C atoms or an alkylene group having 1 to 5 C atoms which forms a ring with $A_2$, and where $R_8$ is hydrogen.

23. The compound of claim 1, wherein said compound has a structure according to the following formula:

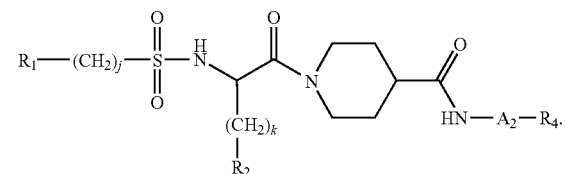

24. The compound of claim 23, wherein said compound has a structure according to the following formula:

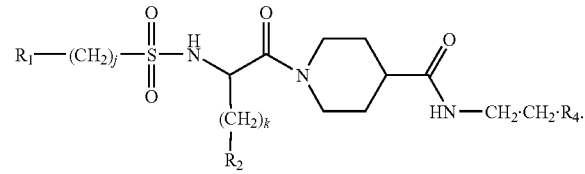

25. The compound of claim 1, wherein said compound has a structure according to the following formula:
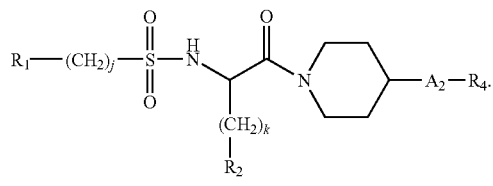
26. The compound of claim 25, wherein said compound has a structure according to a formula selected from the group consisting of:
(a)
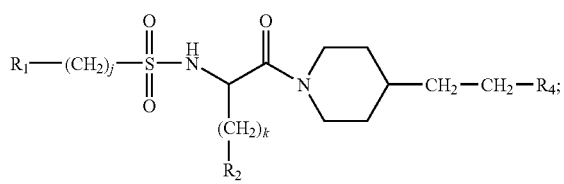
(b)
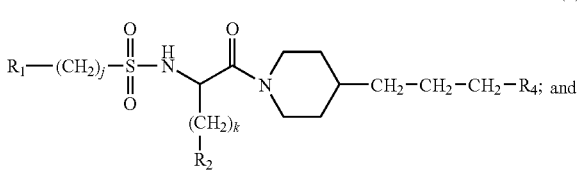
(c)
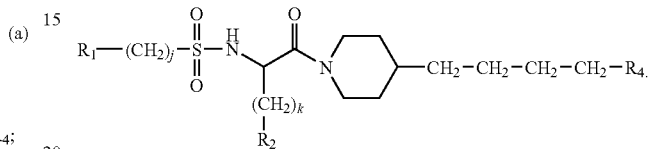
27. The compound of claim 1, wherein said compound is selected from the group consisting of:
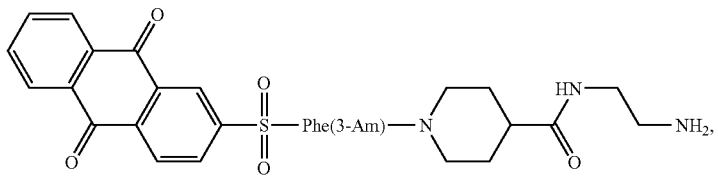
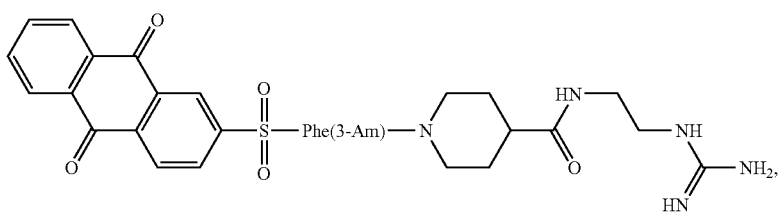
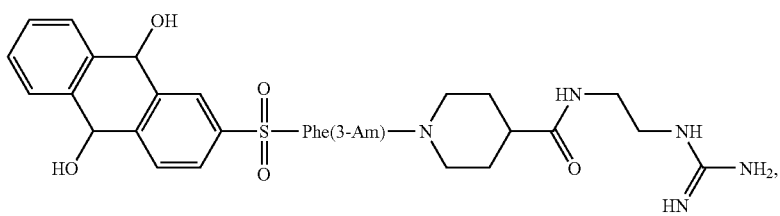
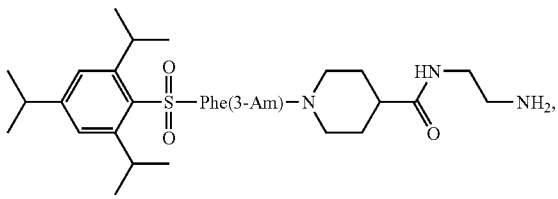
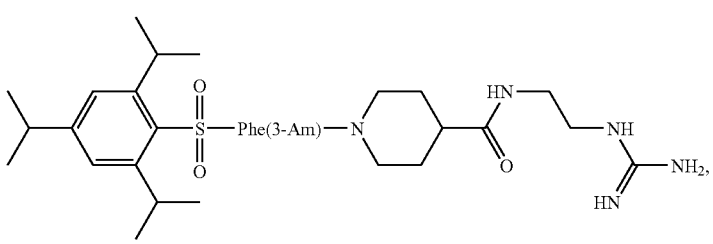

-continued
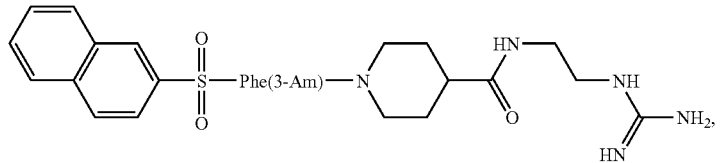
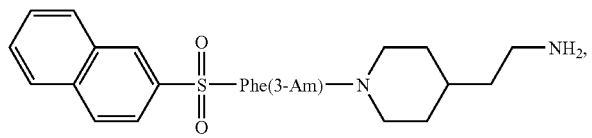
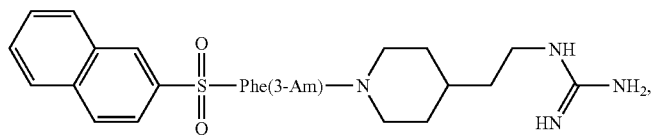
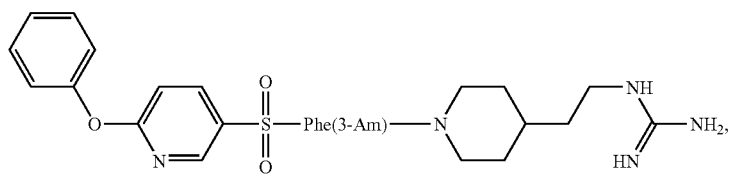
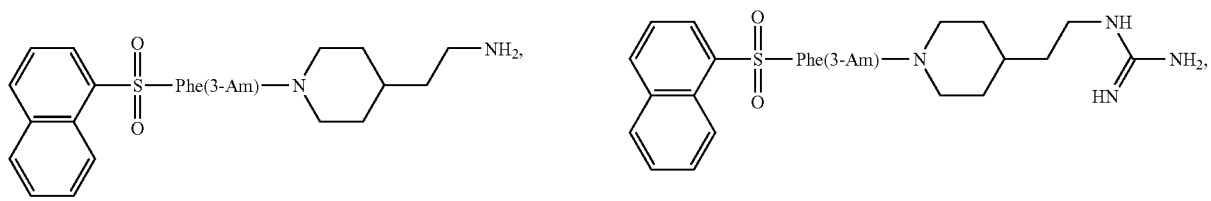
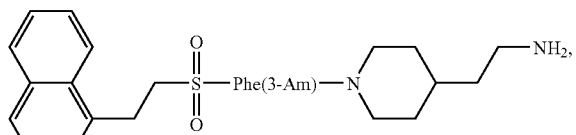
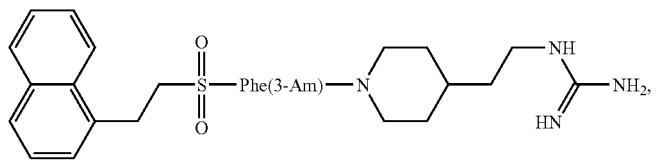
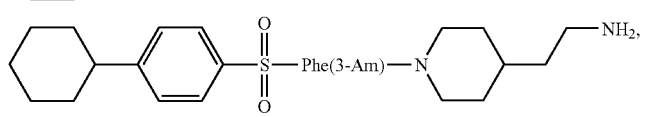
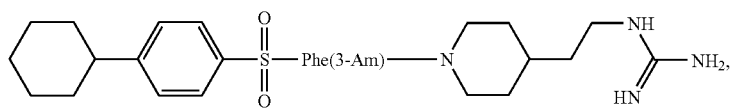
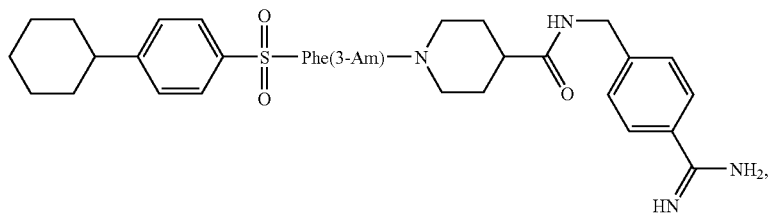

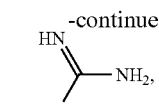
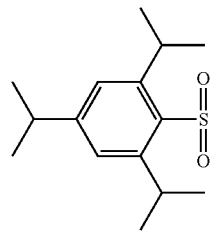
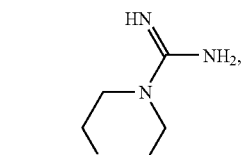
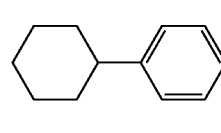
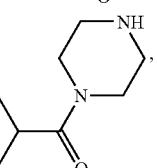
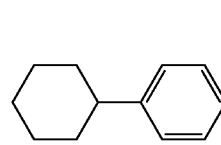
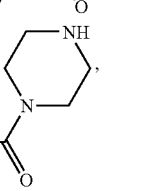
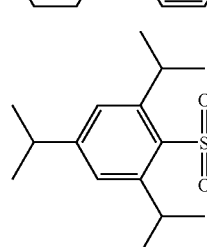
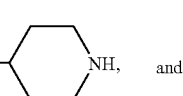
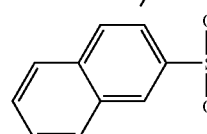
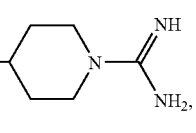
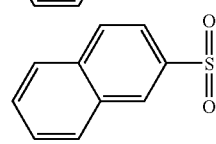
wherein Phe(3-Am) is 3-amidinophenylalanine.
* * * * *

UNITED STATES PATENT AND TRADEMARK OFFICE
CERTIFICATE OF CORRECTION

PATENT NO.        : 7,772,251 B2
APPLICATION NO.   : 10/555821
DATED             : August 10, 2010
INVENTOR(S)       : Stürzebecher et al.

It is certified that error appears in the above-identified patent and that said Letters Patent is hereby corrected as shown below:

Cover Page, under OTHER PUBLICATIONS, in Wilkstroem et al.,
replace "prparation" with --preparation--;

Under OTHER PUBLICATIONS, in Rubini et al., replace "Tetrhedron" with --Tetrahedron--.

Page 2, under OTHER PUBLICATIONS, in Lin et al., replace
"Matrix-Degarding" with --Matrix-Degrading--;

Under OTHER PUBLICATIONS, in Long et al., replace "*Biorganic*" with --*Bioorganic*--;

Under OTHER PUBLICATIONS, in Oberst et al., replace "Inhibitgor" with --Inhibitor--;

Under OTHER PUBLICATIONS, in Takeuchi et al., replace "Biochemisty" with --Biochemistry--;

Under OTHER PUBLICATIONS, "Hooper et al., 'Type II Transmembrane Serine Proteases'" is listed twice. Please remove second reference.

Column 2, Line 2, replace "BANKIt25705.0" with --BANKIt257050--.

Column 19, Line 33, replace "(1)" with --(I)--.

Column 22, Line 3, replace "alia Alkyl" with --alia. Alkyl--;

Line 24, replace "by by" with --by--.

Column 26, Line 54, replace "U.S.A." with --U.S.A..--.

Column 28, Line 24, add --(P1)--.

Signed and Sealed this
Tenth Day of January, 2012

David J. Kappos
*Director of the United States Patent and Trademark Office*

CERTIFICATE OF CORRECTION (continued)
U.S. Pat. No. 7,772,251 B2

Column 29, Line 19, replace "radical R" with --radical $R_4$--;

Line 64, replace "-(C'-O)-NH-," with -- -(C=O)-NH- --.

Column 30, Line 12, replace "(P2)" with --(E3")--;

Line 50, replace "as" with --a--.

Column 33, Line 33, replace "3-(cyanophenylalanine" with --3-(cyano)phenylalanine--.

Column 40, Line 62, replace "5'-GCATGAATTCTTATACCCCAGTTCTCTTTGATCCA-3" with -- 5'GCATGAATTCTTATACCCCAGTGTTCTCTTTGATCCA-3--.

Line 62, replace "3" with --3'--.

Column 42, Line 31, replace "egression" with --linear regression--.

Column 65, Line 26, replace "claim 2" with --claim 1--;

Line 68, replace "(E1')" with --(E1")--.

Column 66, Line 23, replace " $R_2$'" with --$R_2$"--;

Column 66, Lines 54-55, replace "T=(C=O)-NH-," with --T=-(C=O)-NH-,--.